US008916604B2

(12) United States Patent  
Kong

(10) Patent No.: US 8,916,604 B2
(45) Date of Patent: Dec. 23, 2014

(54) COMPOSITIONS AND METHODS FOR EPIGENETIC MODIFICATION OF NUCLEIC ACID SEQUENCES

(75) Inventor: Ah-Ng T. Kong, Whitehouse Station, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 54 days.

(21) Appl. No.: 13/485,100

(22) Filed: May 31, 2012

(65) Prior Publication Data

US 2012/0309808 A1 Dec. 6, 2012

Related U.S. Application Data

(60) Provisional application No. 61/491,683, filed on May 31, 2011.

(51) Int. Cl.
*A61K 31/405* (2006.01)
*A61K 31/16* (2006.01)
*A61K 31/404* (2006.01)
*A61K 31/26* (2006.01)

(52) U.S. Cl.
CPC .............. *A61K 31/26* (2013.01); *A61K 31/404* (2013.01)
USPC ........................................ 514/415; 514/599

(58) Field of Classification Search
CPC ............................ A61K 31/26; A61K 31/404
USPC .................................................. 514/415, 599
See application file for complete search history.

(56) References Cited

U.S. PATENT DOCUMENTS 5,948,808 A * 9/1999 Safe ............................... 514/415

OTHER PUBLICATIONS

Jeong et al., "Differential Expression and Stability of Endogenous Nuclear Factor E2-related Factor 2 (Nrf2) by Natural Chemopreventive Compounds in HepG2 Human Hepatoma Cells", Journal of Biochemistry and Molecular Biology, vol. 38, No. 2, pp. 167-176 (2005).*
Anderton et al., "Physiological modeling of formulated and crystalline 3,3'-diindolylmethane pharmacokinetics following oral administration in mice," Drug Metab Dispos., (2004) vol. 32, pp. 632-638.
Barve et al., "Pharmacogenomic profile of soy isoflavone concentrate in the prostate of Nrf2 deficient and wild-type mice," J Pharm Sci., (2008) vol. 94, pp. 4528-4545 (Abstract only).
Lee et al., "Interaction index and different methods for determining drug interaction in combination therapy," J Biopharm Stat, (2007) vol. 17, pp. 461-480 (Abstract only).
Park et al., "Prostatic Intraepithelial Neoplasia in Genetically Engineered Mice," Am J Pathol., (2002) vol. 161, pp. 727-735.
Saw et al., "Synergistic anti-inflammatory effects of low doses of curcumin in combination with polyunsaturated fatty acids: docosahexaenoic acid or eicosapentaenoic acid," Biochem Pharmacol, (2010) vol. 79, pp. 421-430 (Abstract only).
Xue et al., "3,3'-Diindolylmethane stimulates murine immune function in vitro and in vivo," J Nutr Biochem., (2008) vol. 19, pp. 336-344.

* cited by examiner

*Primary Examiner* — Kevin E Weddington
(74) *Attorney, Agent, or Firm* — Fox Rothschild LLP; Peter J. Butch, III; Wansheng Jerry Liu

(57) ABSTRACT

Provided herein are pharmaceutical compositions and methods for treating disorders characterized by reduced expression of anti-oxidative stress enzymes in a subject. In one aspect, the present invention provides a method for inducing expression of anti-oxidative stress enzymes in a subject in need thereof. The method includes administering to the subject a therapeutically effective amount of a demethylating agent. The demethylating agent includes a phytochemical that induces expression of Nrf2 and Nrf2-mediated genes expressing anti-oxidative stress. Such phytochemicals include indoles, such as 3,3'-diindolylmethane (DIM) and indole-3-carbinol (I3C), and isothiocyanates, such as phenethyl isothiocyanate (PEITC) and sulforaphane (SFN).

8 Claims, 23 Drawing Sheets

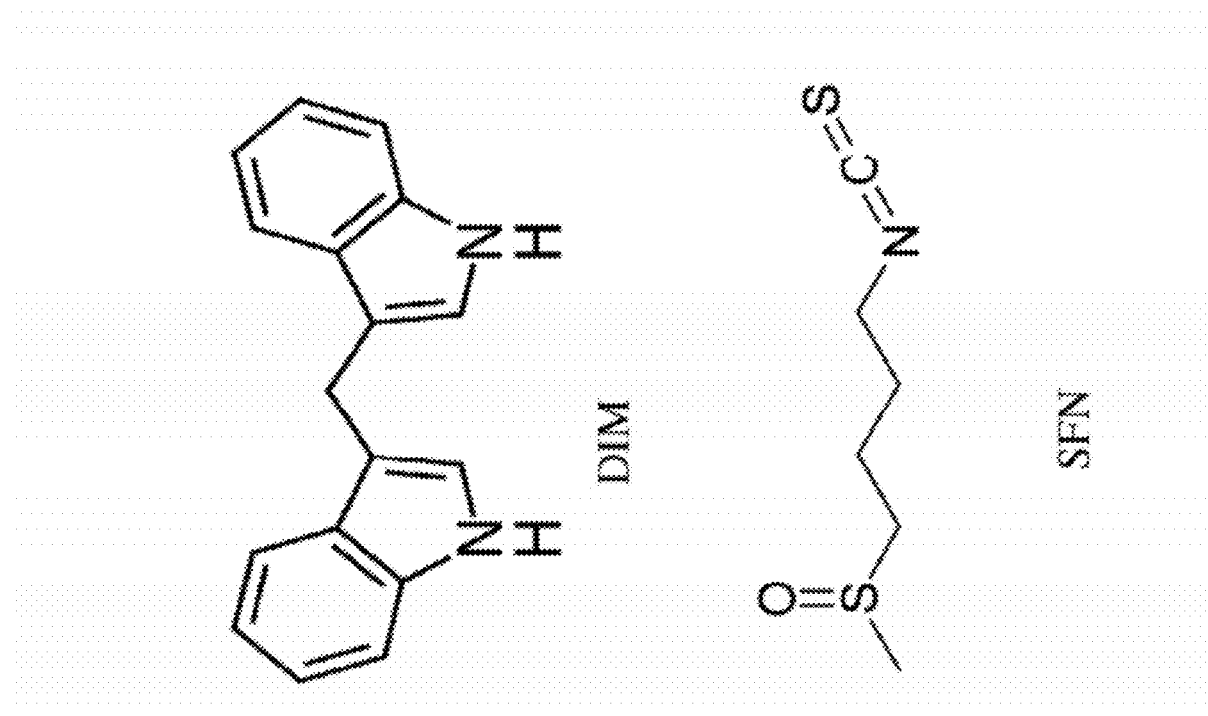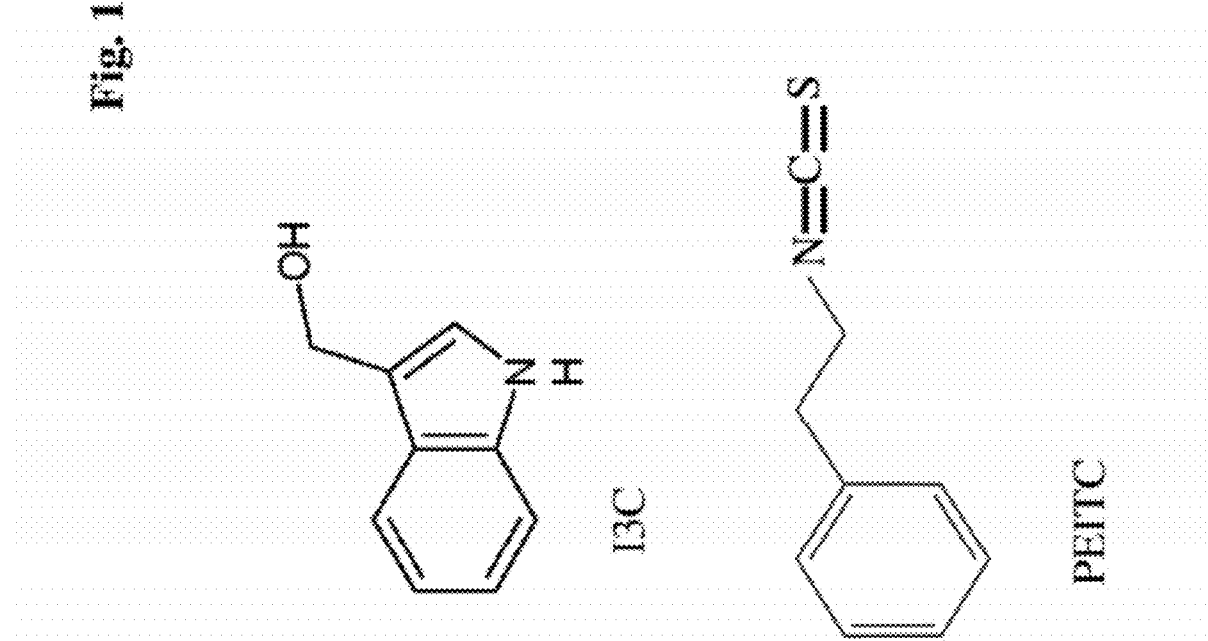
Fig. 1

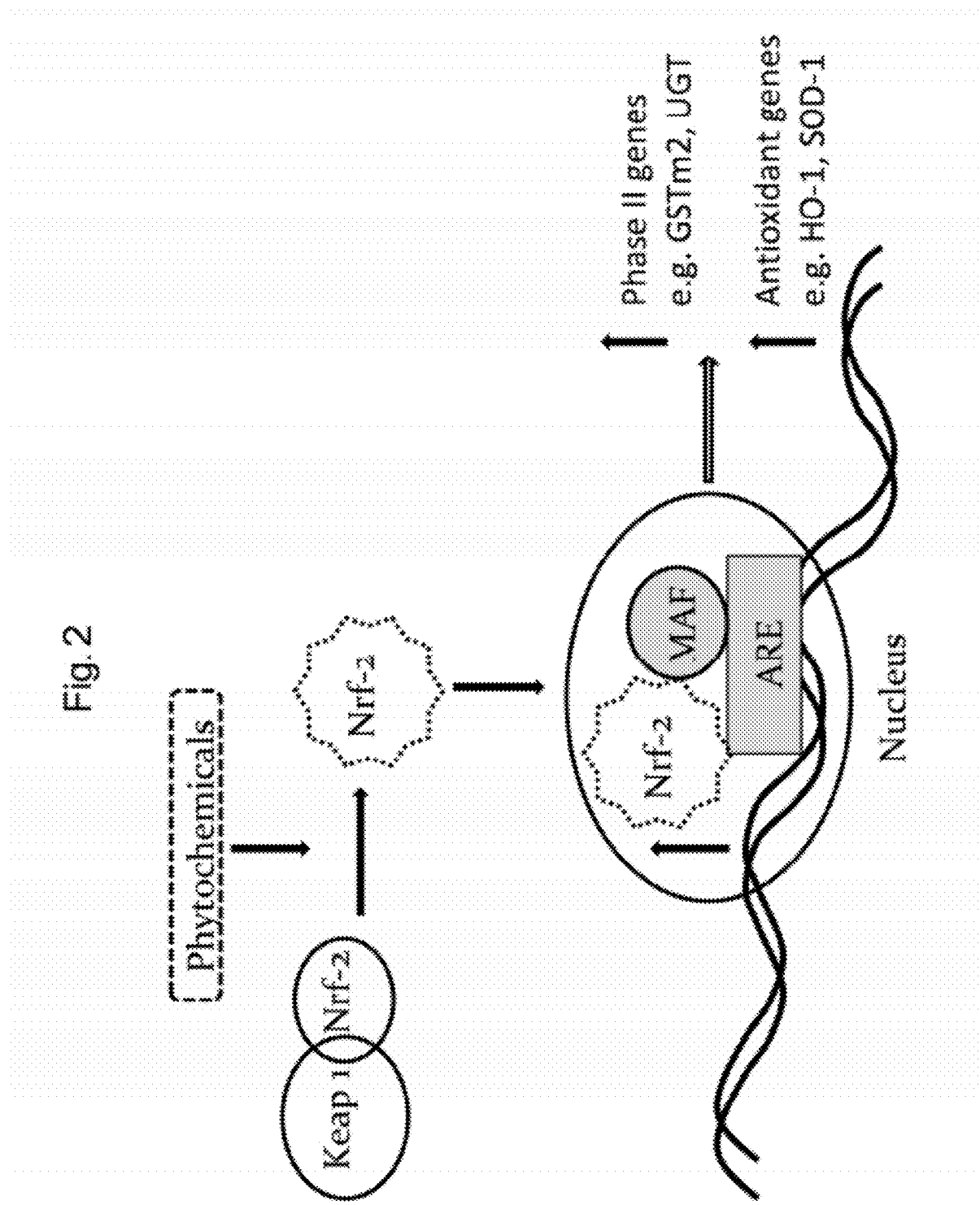

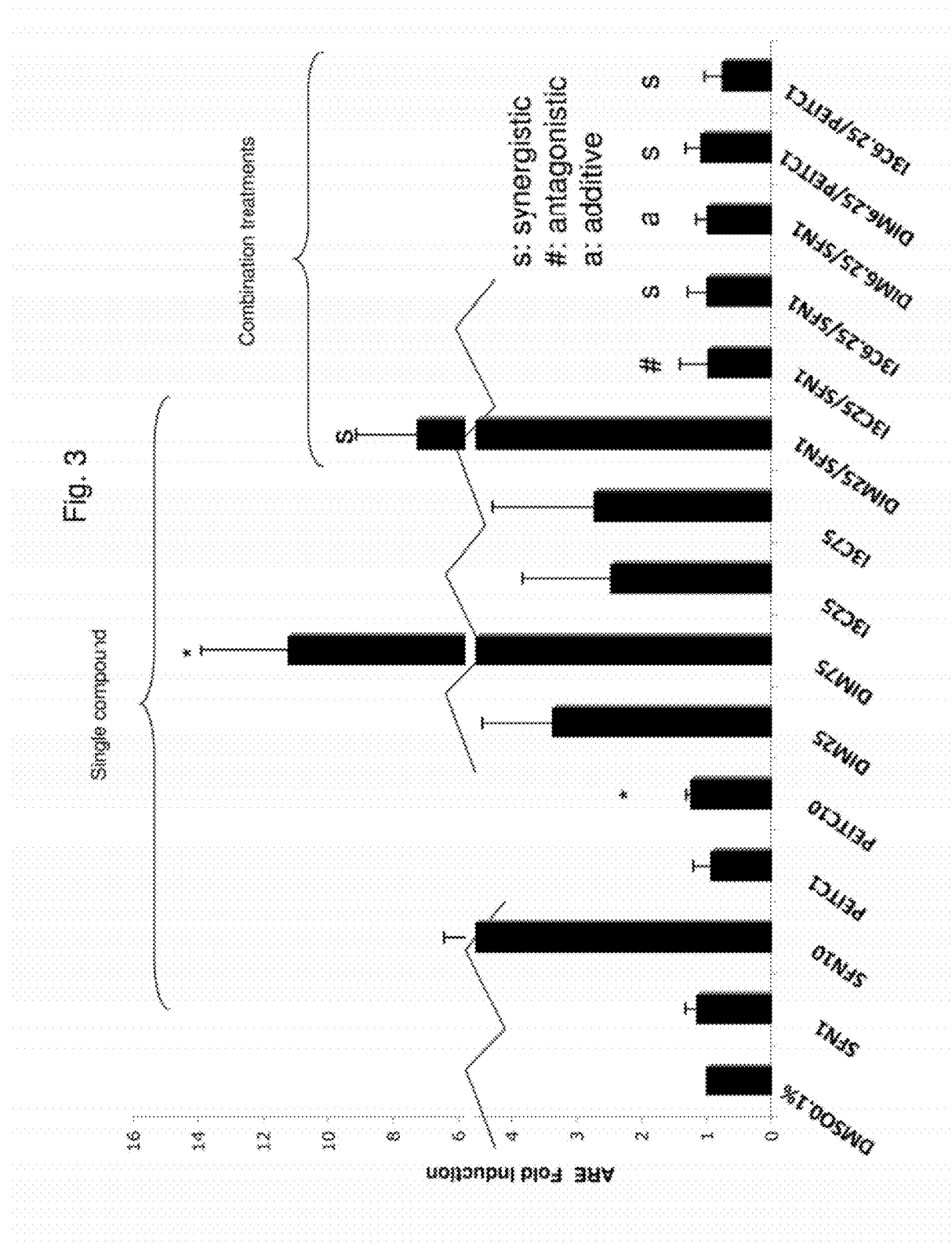

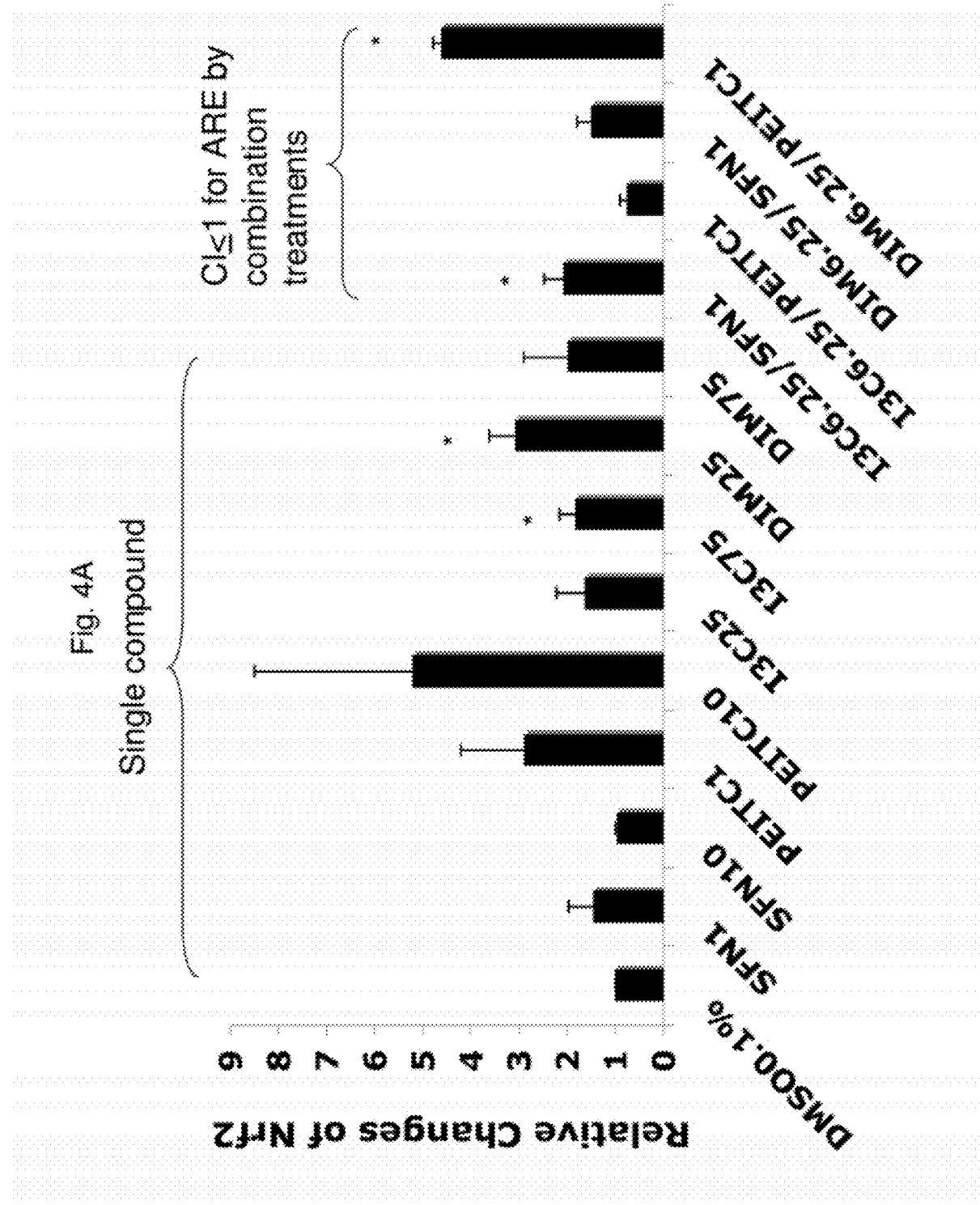

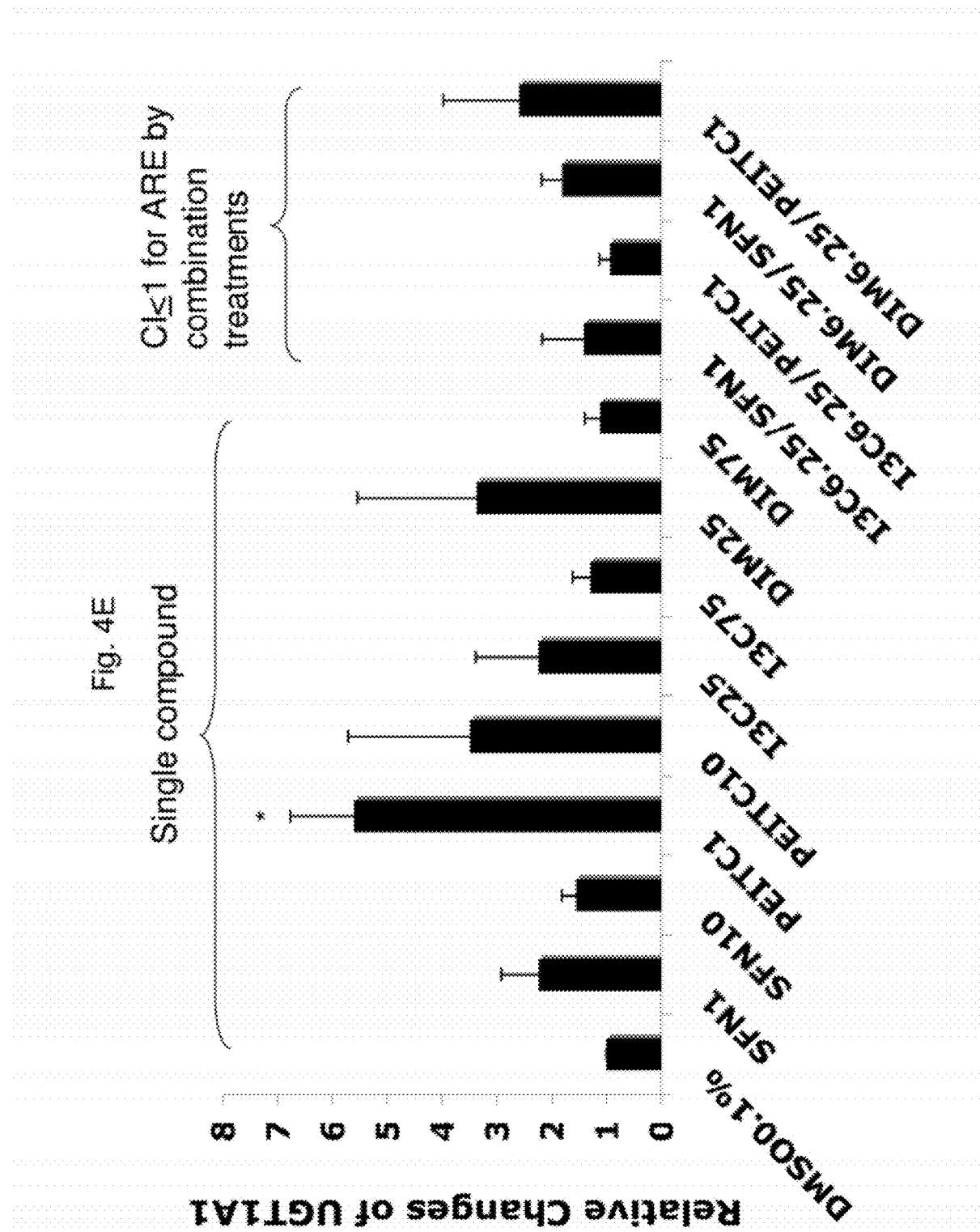

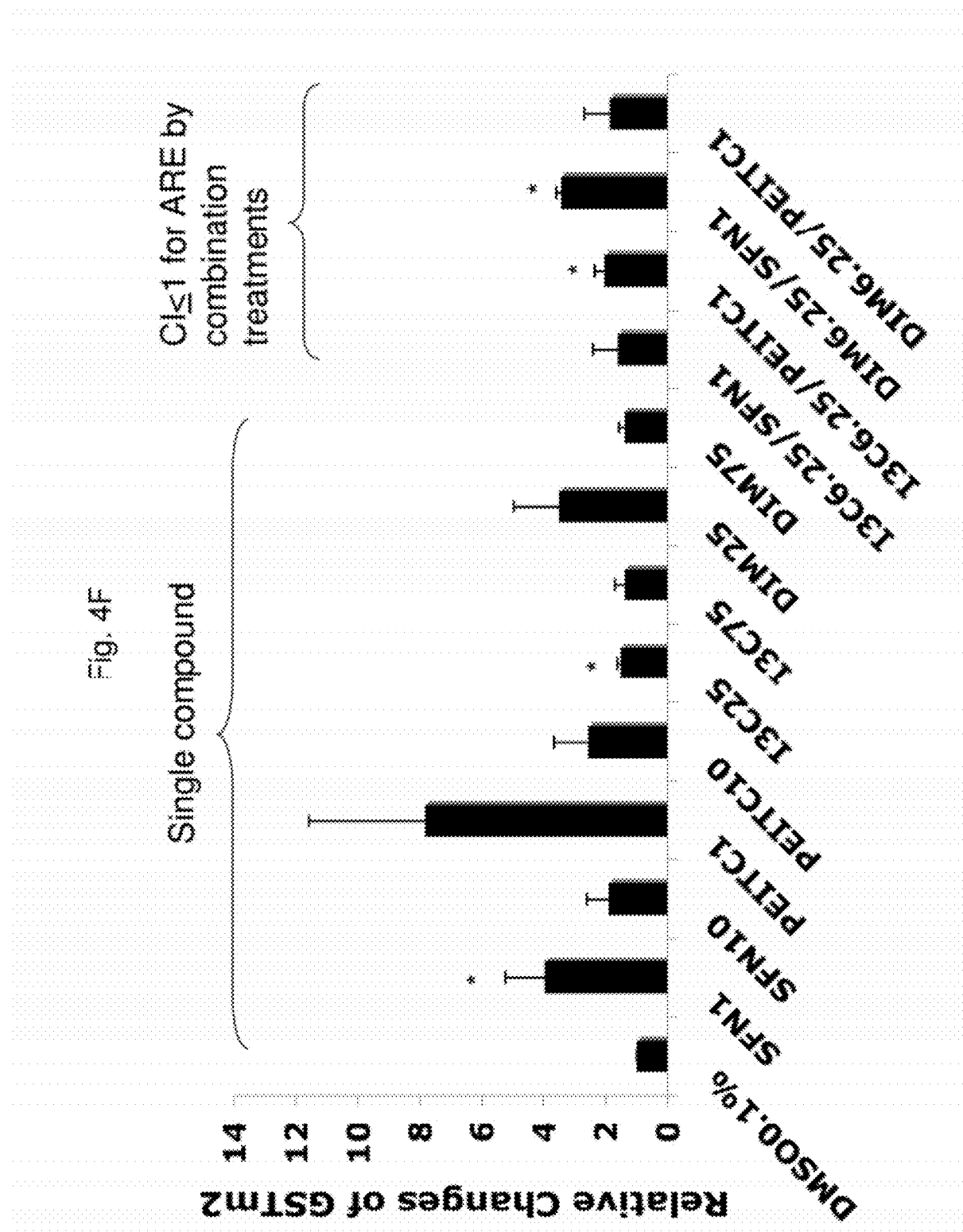

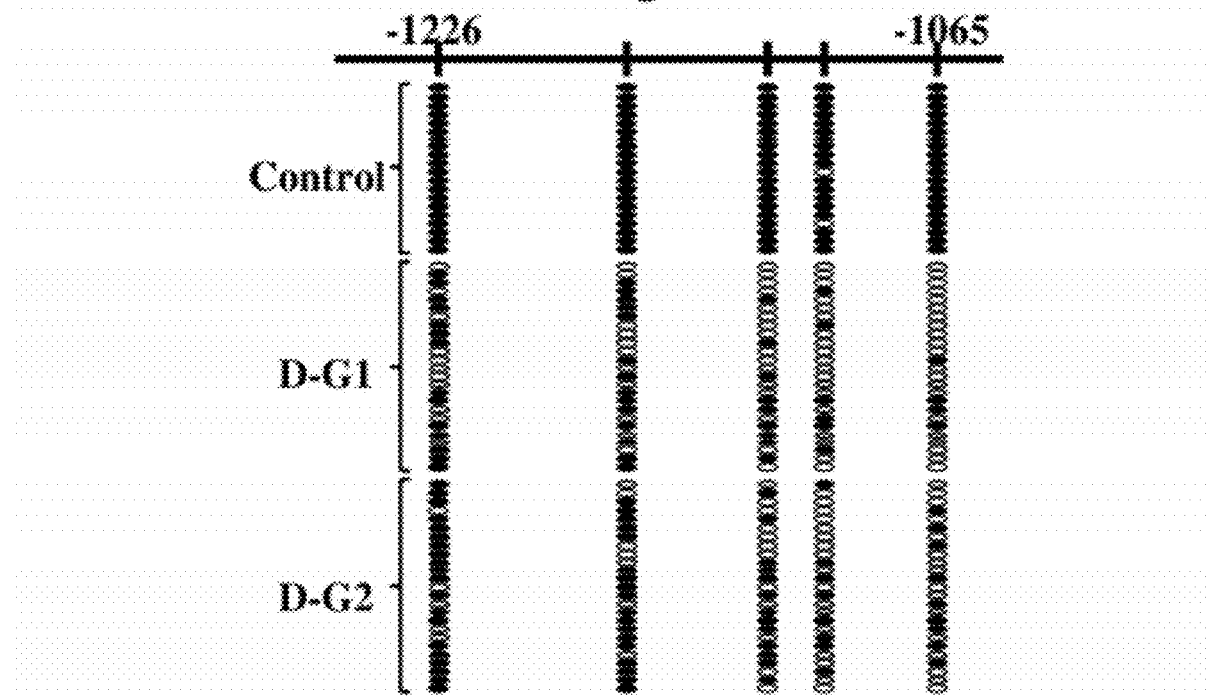
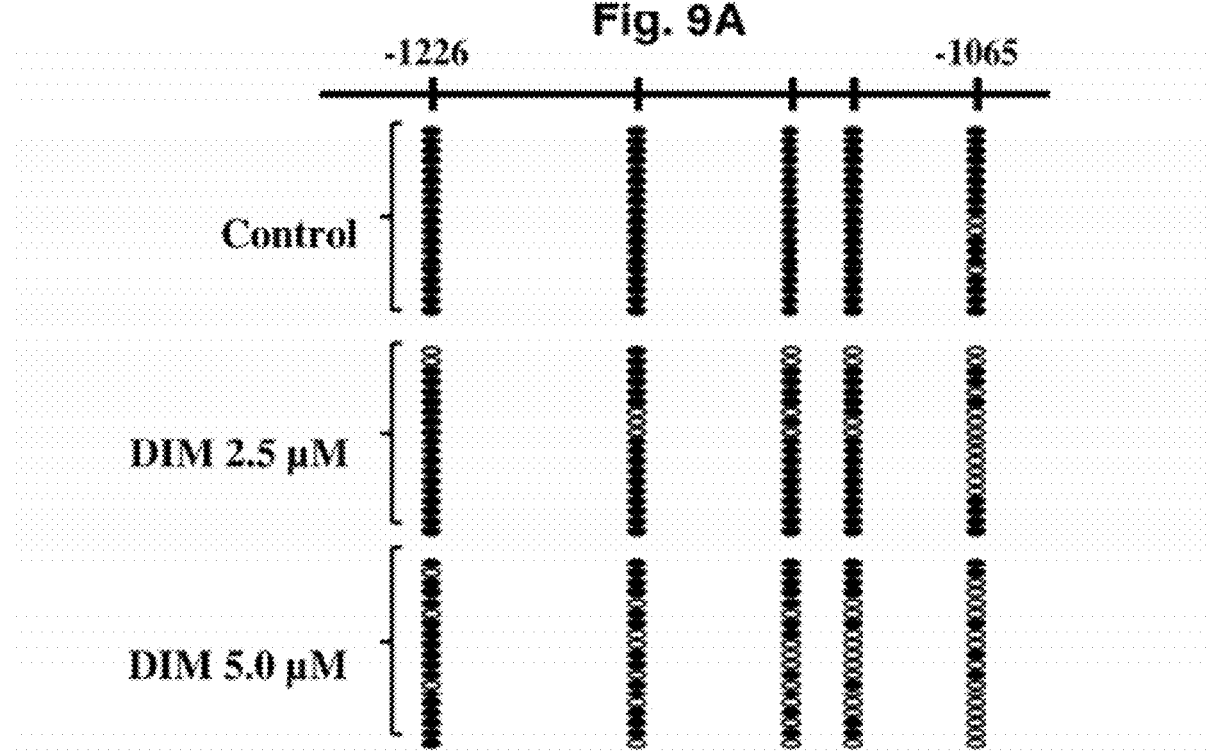

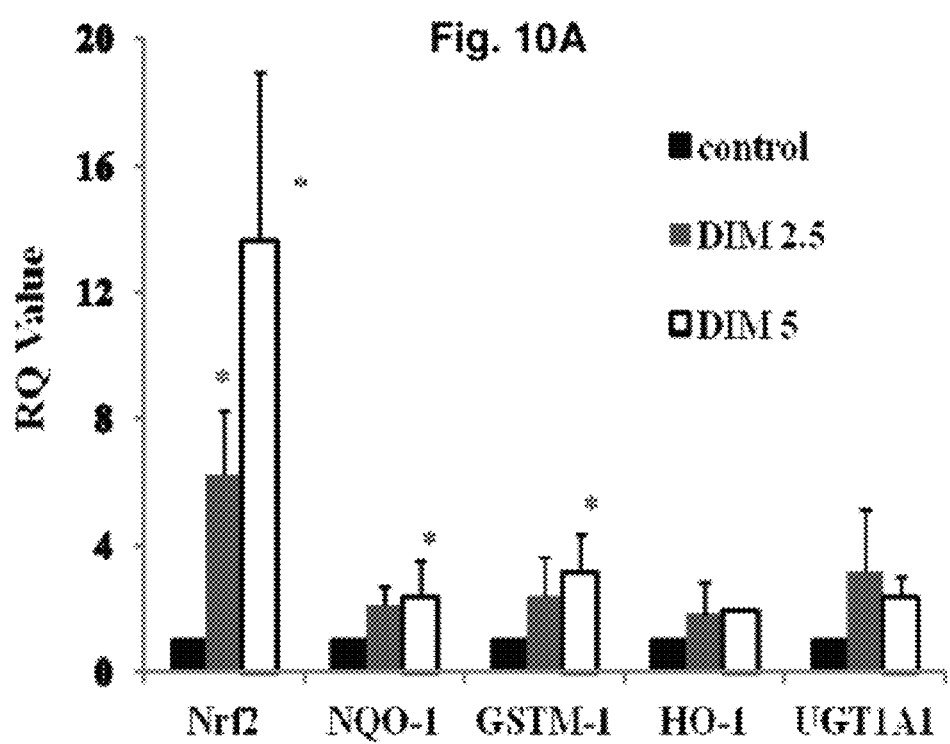

Fig. 10B
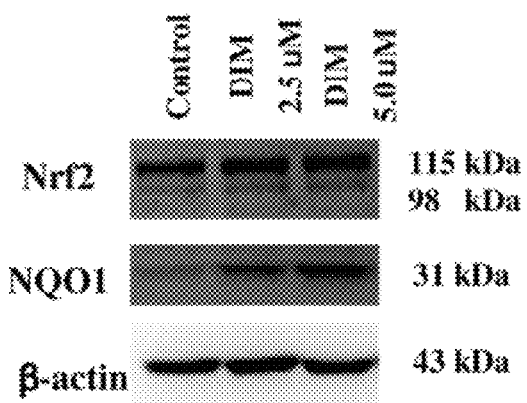
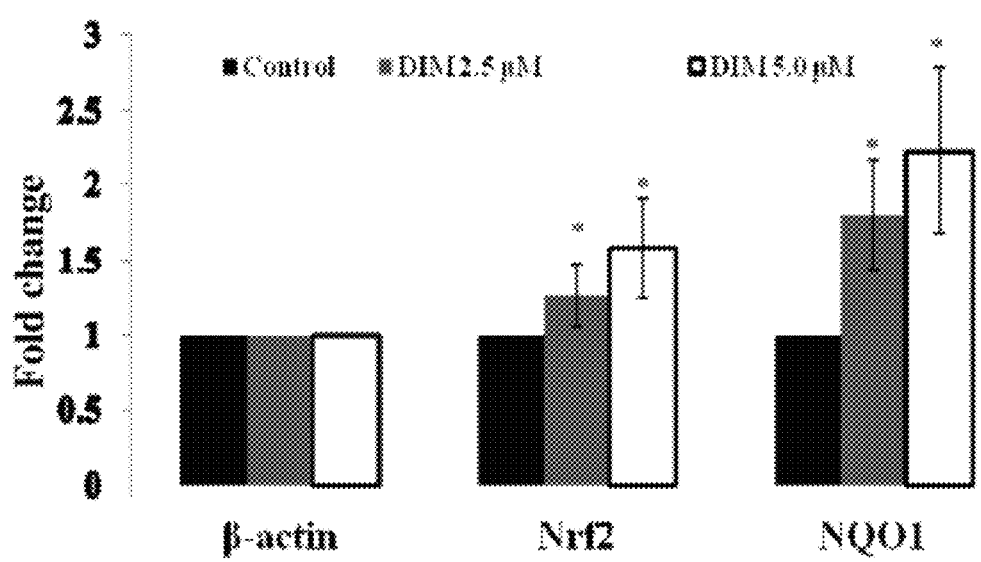

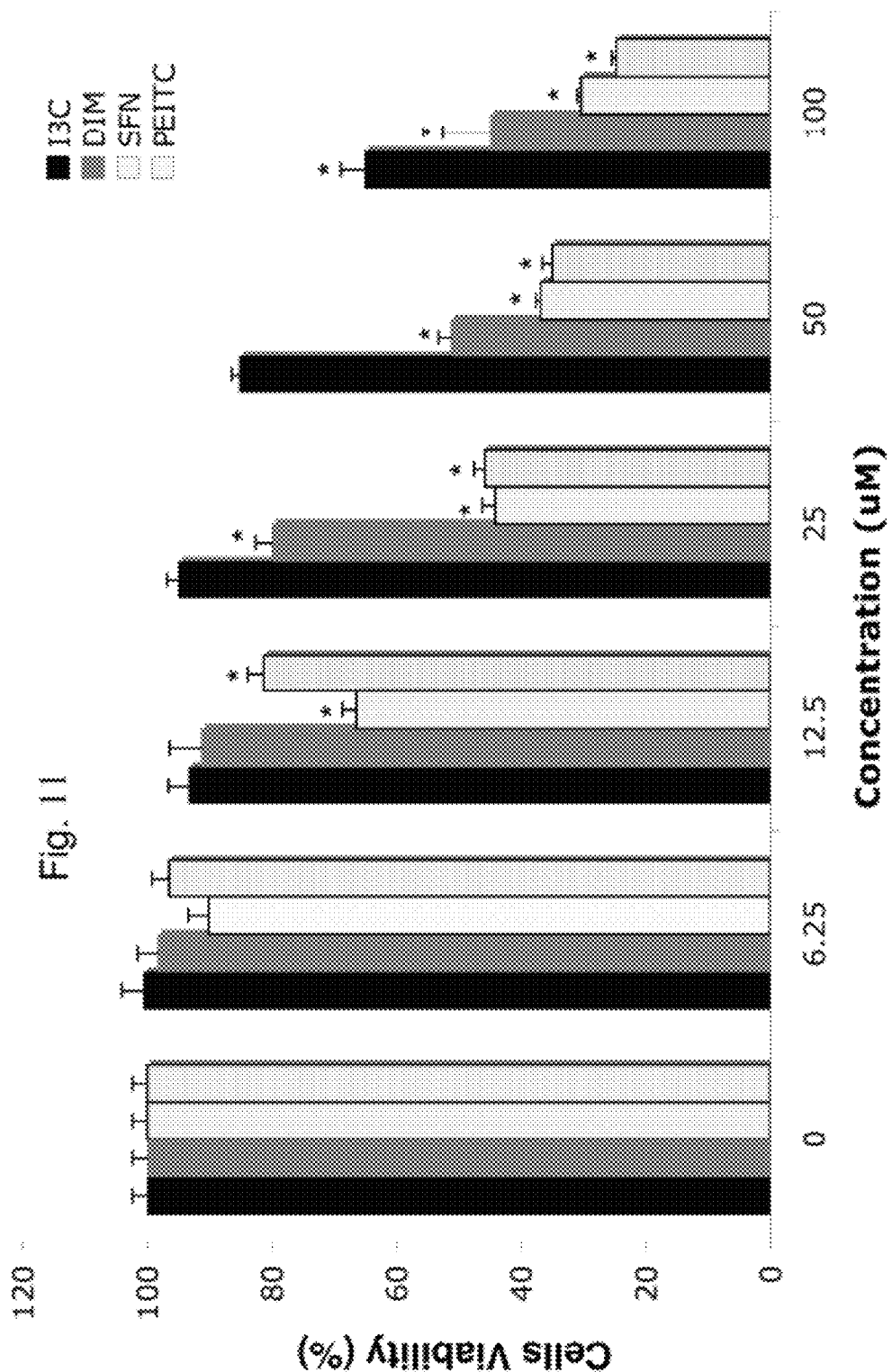

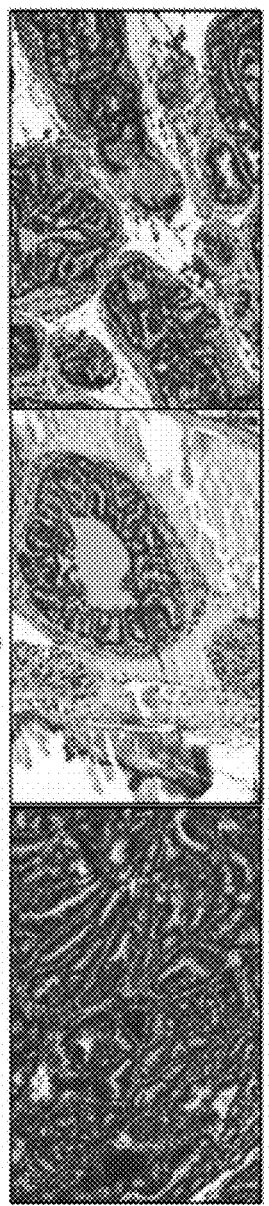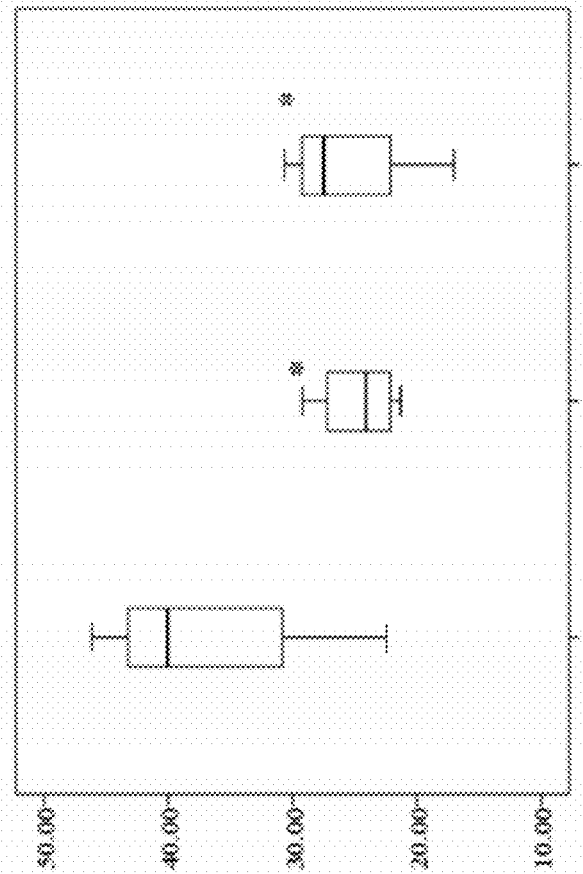

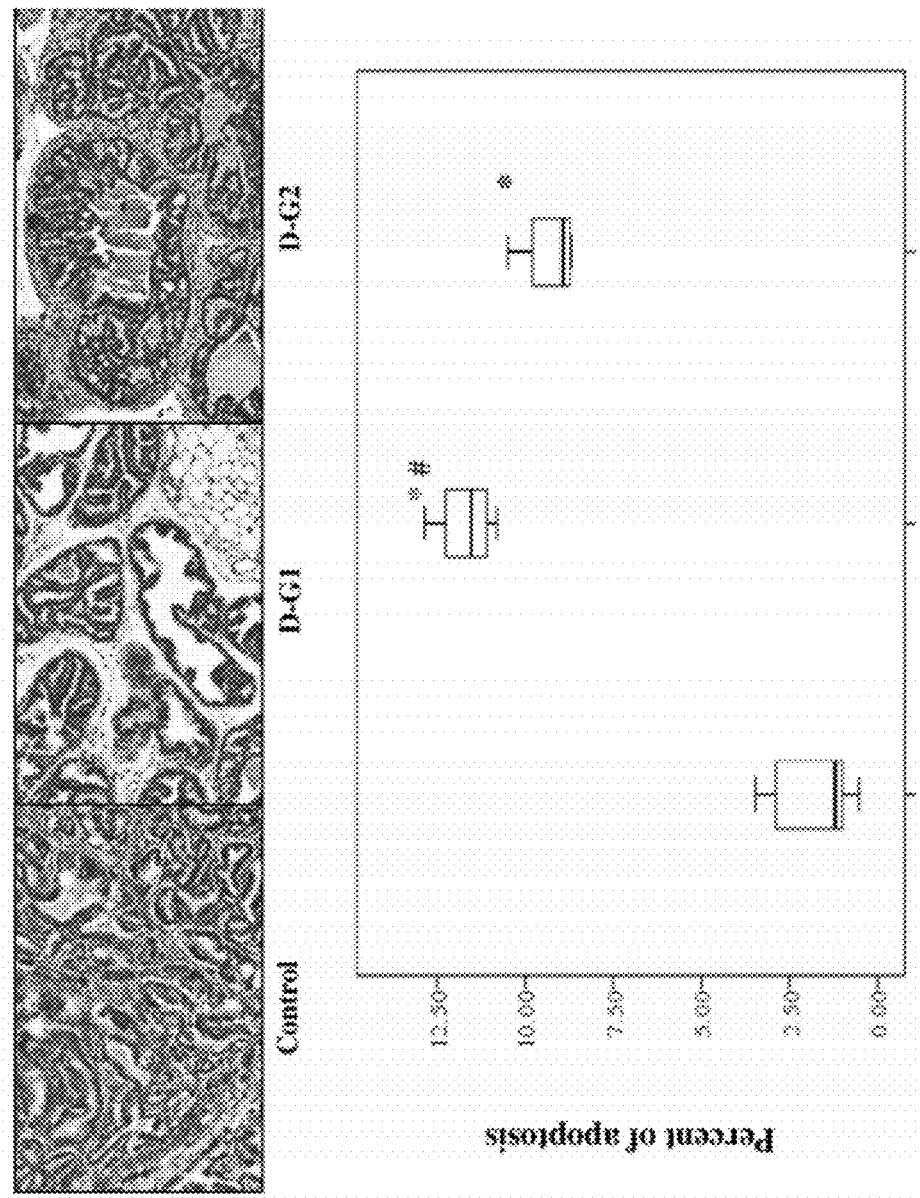

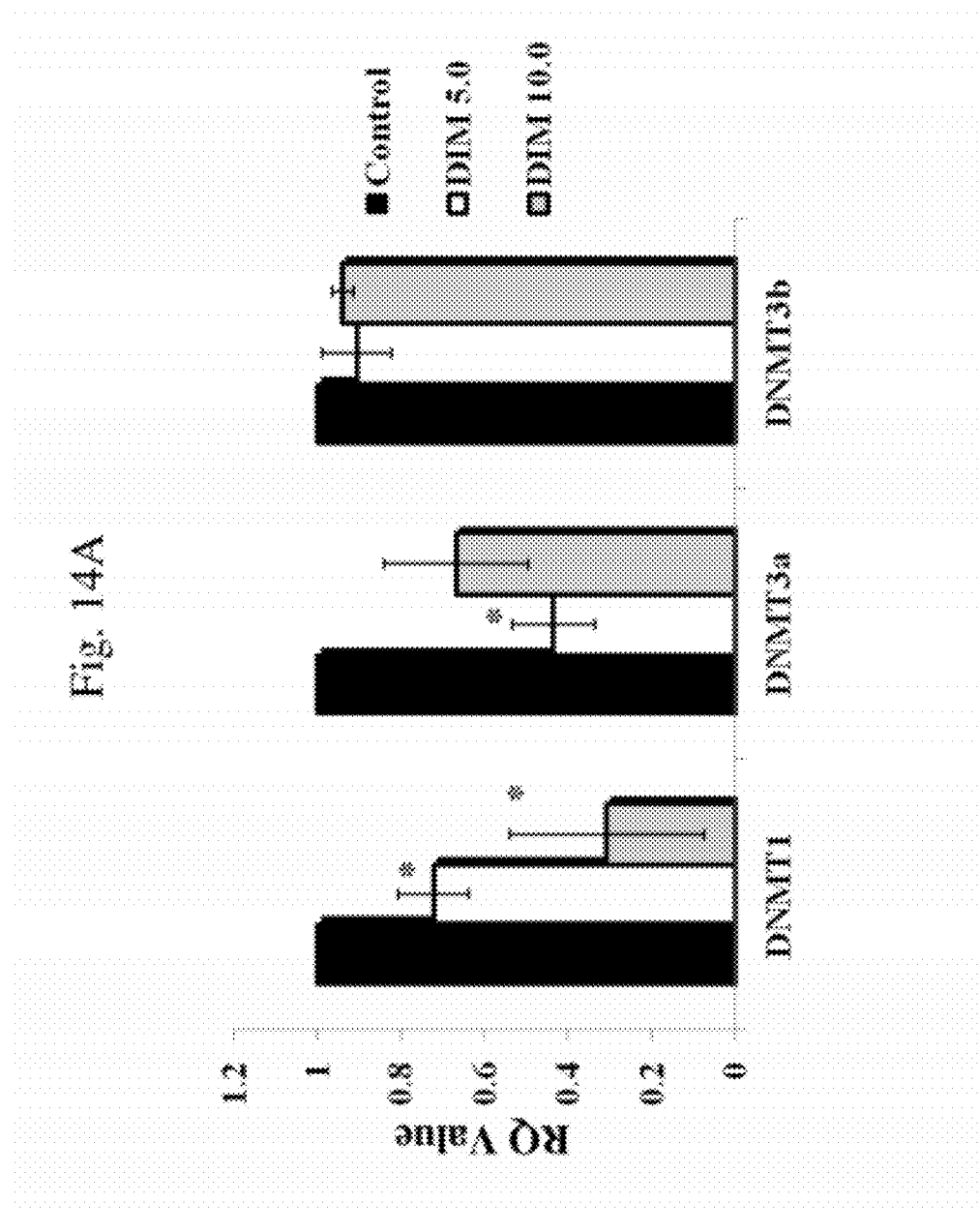

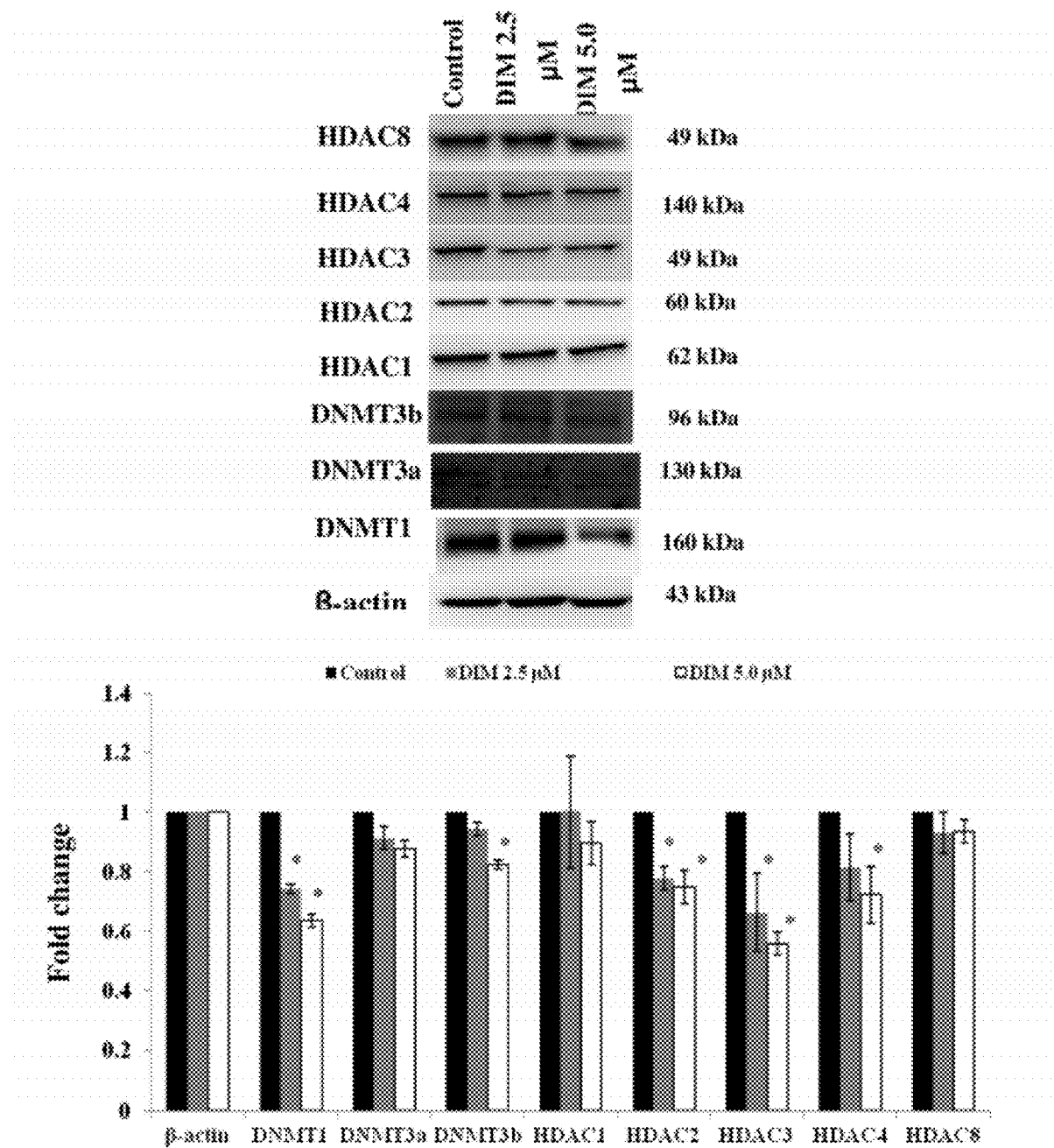

SEQUENCE LISTING

```
<160> NUMBER OF SEQ ID NOS: 40

<210> SEQ ID NO 1
<211> LENGTH: 24
<212> TYPE: DNA
<213> ORGANISM: Artificial
<220> FEATURE:
<223> OTHER INFORMATION: Synthetic Primer

<400> SEQUENCE: 1
tcgacagtca gccgcatctt cttt                                          24

<210> SEQ ID NO 2
<211> LENGTH: 24
<212> TYPE: DNA
<213> ORGANISM: Artificial
<220> FEATURE:
<223> OTHER INFORMATION: Synthetic primer

<400> SEQUENCE: 2
accaaatccg ttgactccga cctt                                          24

<210> SEQ ID NO 3
<211> LENGTH: 24
<212> TYPE: DNA
<213> ORGANISM: Artificial
<220> FEATURE:
<223> OTHER INFORMATION: Synthetic primer

<400> SEQUENCE: 3
actaaagcca gcctgacctt cctt                                          24
```

```
<210> SEQ ID NO 4
<211> LENGTH: 24
<212> TYPE: DNA
<213> ORGANISM: Artificial
<220> FEATURE:
<223> OTHER INFORMATION: Synthetic primer

<400> SEQUENCE: 4
aatgctgctc cttcatgcaa cacg                                              24

<210> SEQ ID NO 5
<211> LENGTH: 24
<212> TYPE: DNA
<213> ORGANISM: Artificial
<220> FEATURE:
<223> OTHER INFORMATION: Synthetic primer

<400> SEQUENCE: 5
acgcgttgta attaagcctc gcac                                              24

<210> SEQ ID NO 6
<211> LENGTH: 24
<212> TYPE: DNA
<213> ORGANISM: Artificial
<220> FEATURE:
<223> OTHER INFORMATION: Synthetic primer

<400> SEQUENCE: 6
ttccgctggt cattaaggct gagt                                              24

<210> SEQ ID NO 7
<211> LENGTH: 24
<212> TYPE: DNA
<213> ORGANISM: Artificial
<220> FEATURE:
<223> OTHER INFORMATION: Synthetic primer

<400> SEQUENCE: 7
aaggatggaa gaaacgcctg gaga                                              24

<210> SEQ ID NO 8
<211> LENGTH: 24
<212> TYPE: DNA
<213> ORGANISM: Artificial
<220> FEATURE:
<223> OTHER INFORMATION: Synthetic primer

<400> SEQUENCE: 8
ggcccacaga aaggccaaat ttct                                              24

<210> SEQ ID NO 9
<211> LENGTH: 24
<212> TYPE: DNA
<213> ORGANISM: Artificial
<220> FEATURE:
<223> OTHER INFORMATION: Synthetic primer

<400> SEQUENCE: 9
tgctttatag cgtgcaaacc tcgc                                              24

<210> SEQ ID NO 10
<211> LENGTH: 24
<212> TYPE: DNA
<213> ORGANISM: Artificial
<220> FEATURE:
```

<223> OTHER INFORMATION: Synthetic primer

<400> SEQUENCE: 10
atccatgtcc cttgacagca caga    24

<210> SEQ ID NO 11
<211> LENGTH: 24
<212> TYPE: DNA
<213> ORGANISM: Artificial
<220> FEATURE:
<223> OTHER INFORMATION: Synthetic primer

<400> SEQUENCE: 11
gcagggcatc atcaatttcg agca    24

<210> SEQ ID NO 12
<211> LENGTH: 24
<212> TYPE: DNA
<213> ORGANISM: Artificial
<220> FEATURE:
<223> OTHER INFORMATION: Synthetic primer

<400> SEQUENCE: 12
tgcaggcctt cagtcagtcc ttta    24

<210> SEQ ID NO 13
<211> LENGTH: 24
<212> TYPE: DNA
<213> ORGANISM: Artificial
<220> FEATURE:
<223> OTHER INFORMATION: Synthetic primer

<400> SEQUENCE: 13
atgacccgtg cctttatcac ccat    24

<210> SEQ ID NO 14
<211> LENGTH: 24
<212> TYPE: DNA
<213> ORGANISM: Artificial
<220> FEATURE:
<223> OTHER INFORMATION: Synthetic primer

<400> SEQUENCE: 14
agtctccatg cgctttgcat tgtc    24

<210> SEQ ID NO 15
<211> LENGTH: 20
<212> TYPE: DNA
<213> ORGANISM: Artificial
<220> FEATURE:
<223> OTHER INFORMATION: Synthetic primer

<400> SEQUENCE: 15
cgttcaatac cccagccatg    20

<210> SEQ ID NO 16
<211> LENGTH: 19
<212> TYPE: DNA
<213> ORGANISM: Artificial
<220> FEATURE:
<223> OTHER INFORMATION: Synthetic primer

<400> SEQUENCE: 16
gaccccgtca ccagagtcc    19

<210> SEQ ID NO 17
<211> LENGTH: 24
<212> TYPE: DNA
<213> ORGANISM: Artificial
<220> FEATURE:
<223> OTHER INFORMATION: Synthetic primer

<400> SEQUENCE: 17
ccaagctccg gaccctggat gtgt                                          24

<210> SEQ ID NO 18
<211> LENGTH: 24
<212> TYPE: DNA
<213> ORGANISM: Artificial
<220> FEATURE:
<223> OTHER INFORMATION: Synthetic primer

<400> SEQUENCE: 18
cgaggccggt agtagtcaca gtag                                          24

<210> SEQ ID NO 19
<211> LENGTH: 25
<212> TYPE: DNA
<213> ORGANISM: Artificial
<220> FEATURE:
<223> OTHER INFORMATION: Synthetic primer

<400> SEQUENCE: 19
gcacctatgg gctgctgcga agacg                                         25

<210> SEQ ID NO 20
<211> LENGTH: 25
<212> TYPE: DNA
<213> ORGANISM: Artificial
<220> FEATURE:
<223> OTHER INFORMATION: Synthetic primer

<400> SEQUENCE: 20
ctgcctccaa tcaccaggtc gaatg                                         25

<210> SEQ ID NO 21
<211> LENGTH: 22
<212> TYPE: DNA
<213> ORGANISM: Artificial
<220> FEATURE:
<223> OTHER INFORMATION: Synthetic primer

<400> SEQUENCE: 21
gtctgcacac cagagaccag ag                                            22

<210> SEQ ID NO 22
<211> LENGTH: 23
<212> TYPE: DNA
<213> ORGANISM: Artificial
<220> FEATURE:
<223> OTHER INFORMATION: Synthetic primer

<400> SEQUENCE: 22
tcagagccat tcccatcatc tac                                           23

<210> SEQ ID NO 23
<211> LENGTH: 20
<212> TYPE: DNA
<213> ORGANISM: Artificial
<220> FEATURE:
<223> OTHER INFORMATION: Synthetic primer

<400> SEQUENCE: 23
agcaggacat ggagcaagtt                                            20

<210> SEQ ID NO 24
<211> LENGTH: 20
<212> TYPE: DNA
<213> ORGANISM: Artificial
<220> FEATURE:
<223> OTHER INFORMATION: Synthetic primer

<400> SEQUENCE: 24 ttcttttcc agcgaggaga                                             20

<210> SEQ ID NO 25
<211> LENGTH: 19
<212> TYPE: DNA
<213> ORGANISM: Artificial
<220> FEATURE:
<223> OTHER INFORMATION: Synthetic primer

<400> SEQUENCE: 25
agcccagata ttgtggccg                                             19

<210> SEQ ID NO 26
<211> LENGTH: 20
<212> TYPE: DNA
<213> ORGANISM: Artificial
<220> FEATURE:
<223> OTHER INFORMATION: Synthetic primer

<400> SEQUENCE: 26
cctttcagaa tggctggcac                                            20

<210> SEQ ID NO 27
<211> LENGTH: 21
<212> TYPE: DNA
<213> ORGANISM: Artificial
<220> FEATURE:
<223> OTHER INFORMATION: Synthetic primer

<400> SEQUENCE: 27
cccaccaagt tcaaacagct c                                          21

<210> SEQ ID NO 28
<211> LENGTH: 20
<212> TYPE: DNA
<213> ORGANISM: Artificial
<220> FEATURE:
<223> OTHER INFORMATION: Synthetic primer

<400> SEQUENCE: 28
aggaaggggg tcttagcctc                                            20

<210> SEQ ID NO 29
<211> LENGTH: 24
<212> TYPE: DNA
<213> ORGANISM: Artificial
<220> FEATURE:
<223> OTHER INFORMATION: Synthetic primer

<400> SEQUENCE: 29
ttgttctgcc cacgtttctc tagt                                       24

<210> SEQ ID NO 30
<211> LENGTH: 24

<212> TYPE: DNA
<213> ORGANISM: Artificial
<220> FEATURE:
<223> OTHER INFORMATION: Synthetic primer

<400> SEQUENCE: 30
tctcaaactg gattcagcag gact                                        24

<210> SEQ ID NO 31
<211> LENGTH: 24
<212> TYPE: DNA
<213> ORGANISM: Artificial
<220> FEATURE:
<223> OTHER INFORMATION: Synthetic primer

<400> SEQUENCE: 31
gaaattgctg aggctttggg caga                                        24

<210> SEQ ID NO 32
<211> LENGTH: 24
<212> TYPE: DNA
<213> ORGANISM: Artificial
<220> FEATURE:
<223> OTHER INFORMATION: Synthetic primer

<400> SEQUENCE: 32
atgggagcca gagtgtgtga tgaa                                        24

<210> SEQ ID NO 33
<211> LENGTH: 20
<212> TYPE: DNA
<213> ORGANISM: Artificial
<220> FEATURE:
<223> OTHER INFORMATION: Synthetic primer

<400> SEQUENCE: 33
caaatgttgc ttgtctggtg                                             20

<210> SEQ ID NO 34
<211> LENGTH: 20
<212> TYPE: DNA
<213> ORGANISM: Artificial
<220> FEATURE:
<223> OTHER INFORMATION: Synthetic primer

<400> SEQUENCE: 34
gtcagtcgag tgcacagttt                                             20

<210> SEQ ID NO 35
<211> LENGTH: 23
<212> TYPE: DNA
<213> ORGANISM: Artificial
<220> FEATURE:
<223> OTHER INFORMATION: Synthetic primer

<400> SEQUENCE: 35 ggacaaaacca caactatgca gtg                                        23

<210> SEQ ID NO 36
<211> LENGTH: 21
<212> TYPE: DNA
<213> ORGANISM: Artificial
<220> FEATURE:
<223> OTHER INFORMATION: Synthetic primer

<400> SEQUENCE: 36

```
cagagcagaa ttgtggagtg g                                              21

<210> SEQ ID NO 37
<211> LENGTH: 22
<212> TYPE: DNA
<213> ORGANISM: Artificial
<220> FEATURE:
<223> OTHER INFORMATION: Synthetic primer

<400> SEQUENCE: 37
agttatgaag tagtagtaaa aa                                             22

<210> SEQ ID NO 38
<211> LENGTH: 23
<212> TYPE: DNA
<213> ORGANISM: Artificial
<220> FEATURE:
<223> OTHER INFORMATION: Synthetic primer

<400> SEQUENCE: 38
aatataatct cataaaaccc cac                                            23

<210> SEQ ID NO 39
<211> LENGTH: 20
<212> TYPE: DNA
<213> ORGANISM: Artificial
<220> FEATURE:
<223> OTHER INFORMATION: Synthetic primer

<400> SEQUENCE: 39
gaggtcacca caacacgaac                                                20

<210> SEQ ID NO 40
<211> LENGTH: 20
<212> TYPE: DNA
<213> ORGANISM: Artificial
<220> FEATURE:
<223> OTHER INFORMATION: Synthetic primer

<400> SEQUENCE: 40
atctcataag gccccacctc                                                20
```

COMPOSITIONS AND METHODS FOR EPIGENETIC MODIFICATION OF NUCLEIC ACID SEQUENCES

CROSS REFERENCES TO RELATED APPLICATIONS

This application claims priority under 35 U.S.C. §119(e) to U.S. Application No. 61/491,683, filed on May 31, 2011, the disclosure of which is incorporated herein by reference in its entirety.

STATEMENT REGARDING FEDERALLY FUNDED RESEARCH

This invention was made with government support under grant number R01-CA094828 awarded by the National Institutes of Health. The government has certain rights in the invention.

FIELD OF INVENTION

The present invention relates to the field of epigenetic modification of genomic DNA in mammalian cells. In particular, the present invention relates to methods and compositions for controlling methylation of genomic DNA in mammalian cells.

BACKGROUND

Epigenetic modifications, including chromatin structure modification, DNA and histones covalent and non-covalent modification, nucleosome and small non-coding RNAs remodeling, are fundamental in controlling the normal development and maintenance of gene expression. Epigenetic alteration in general infers changes of gene expression, which is reversible and heritable, without altering the DNA sequence. The onset of diseases have been identified to be associated with abnormal epigenetic regulation. For example, aberrant. DNA methylation in the promoter regions of tumor suppressor genes plays a critical role in cancer development and progression.

DNA methylation, the addition of a methyl group to the fifth carbon position of a cytosine residue by DNA methyltransferase (DNMT), occurs in CpG dinucleotides and is a key epigenetic feature of the human genome. These dinucleotides are usually distributed within stretches of 1- to 2-kb GC-rich DNA, named CpG islands, located in the promoter and/or first exon of 60% of human genes. Promoter methylation is known to participate in reorganizing chromatin structure and also plays a role in transcriptional inactivation.

Hypermethylation of promoters of tumor suppressor genes such as ESR1 (estrogen receptor α) in colorectal and breast cancers, GSTP1 (glutathione S-transferase) in breast and prostate cancers, RARβ2 (retinoid acid receptor β2) in colorectal, breast and prostate cancers, DAPK1 (death-associated protein kinase 1) in breast and lung cancers, have been linked to cancer development and progression in human. Prostate cancer (PCa) is the most commonly diagnosed male cancer (⅙ men in their lifetime) and the second leading cancer related death in men in the USA. Prostate cancer has a very long latency period involving a cascade of epigenetic and genetic changes. Epidemiological, experimental, preclinical, and clinical studies have shown that long-term oxidative stress and chronic inflammatory status would drive the development and progression of PCa.

When cells are exposed to excessive oxidative stress, DNA goes through oxidative damage. When coupled with chronic inflammation and with formation of DNA adducts, this leads to enhanced genomic instability, neoplastic transformation and ultimately drives cancer formation and tumorigenesis. To counteract oxidative stress, induction of various cellular protective enzymes including phase II drug metabolizing enzymes (DME), phase III transporters and antioxidant enzymes occur. Carcinogens are typically metabolized via oxidation and reduction by phase I DME. The resulting products subsequently undergo phase II conjugations catalyzed by phase II DME enzymes such as glutathione S-transferases (GST) and UDP-glucuronosyltransferases (UGT), resulting in the formation of metabolic products which are more water soluble and can be easily excreted in the urine and the bile.

The induction of phase II enzymes can be largely attributed to the transcriptional control of the antioxidant response element by the nuclear factor (erythroid-derived 2)-like 2 (NFE2L2 or Nrf2). Nrf2 is known as a key regulator of the antioxidant response element (ARE)-mediated gene expression and therefore a potential target for cancer chemopreventive compounds. Nrf2 is inhibited in the cytoplasm by the anchor protein Kelch-like ECH-associated protein-1 (Keap1) and in the presence of oxidative stress or chemical inducers. Nrf2 is released from Keap1 inhibition, translocates to the nucleus, dimerizes with small dais and binds to ARE consensus sequence. Regulation of Nrf2 by cancer chemopreventive agents would lead to the induction of gene expression of phase H and anti-oxidative stress enzymes such as heme oxygenase 1 (HO-1). HO-1 catalyzes the degradation of heme to carbon monoxide, iron and biliverdin. HO-1 is critically essential in cellular defensive mechanisms and is implicated with various pathophysiological conditions such as inflammation, atherosclerosis, neurodegenerative diseases and cancers.

Phytochemicals, such as indoles and isothiocyanates (ITCs) possess potent chemopreventive effects. Previous studies show that the indoles achieve the chemopreventive effects via multi-targets. Interest on the dietary indoles has moved beyond preclinical testing and most recently, oral DIM of 2 mg/kg/day has been found to be well tolerated with no significant toxicity. Similarly, oral I3C is also well tolerated. Increasing evidence from in vitro, in vivo and clinical studies have supported the rational use of multi-targeted therapies for cancer treatment and prevention, as well as administration of combinations of conventional chemotherapeutic agents with natural phytochemicals. Indoles are capable of inducing antioxidant activity, regulate cellular proliferative genes, induce cell cycle arrest/apoptosis, regulate hormone metabolism and stimulate the immune system. ITCs also elicit their chemopreventive effects via various mechanisms such as regulating DME phase I cytochrome P450s and phase II, regulating Nrf2-Keap1 signaling and anti-inflammatory NFkB pathways, and inducing cell cycle arrest/apoptosis.

Clinically, advanced and metastasized cancers in humans are very tough to treat, resistant to radiation and chemotherapy because of too numerous epigenetics, genetics and loss of heterozygocity (LOH), among others. Hence it would be logical and clinically feasible if one could utilize relatively non-toxic dietary phytochemicals and or medicinal drugs such as NSAIDs, to prevent, block or delay the progression of benign tumors from becoming advanced/metastasized cancers. Increasing evidence suggests, for example, that during prostatic carcinogenesis, epigenetic changes arise earlier than genetic defects, linking the appearance of epigenetic alterations in some way to disease etiology.

Many relatively non-toxic dietary phytochemicals such as polyphenols from green tea and isothiocyanates from plant food have been shown to inhibit cancer development via epigenetic mechanisms both in vivo and in vitro. Recently, curcumin. a potent anti-cancer agent in many cancer models including PCa, has been found to suppress the expression of DNA methyltransferase (DNMT) and histone deacetylase (HDAC) in the human prostate LNCaP cells and reverses the DNA CpG hypermethylation of the promoter region of Nrf2 in TRAMP C1 cells and Neurog1 in LNCaP cells.

Cruciferous vegetables contain abundant phytochemicals with superior potential in cancer chemopreventive activities. Cruciferous vegetables include broccoli, Brussels sprouts, cabbage and cauliflower and are rich in glucosinolates that can endogenously be converted into compounds including indoles indole-3-carbinol (I3C) and 3,3'-diindolylmethane (DIM)) and ITCs phenethyl isothiocyanate (PEITC) and sulforaphane (SFN)) upon ingestion.

Applicants have recognized, however, that there is a need in the art to understand the mechanism by which indoles (I3C and DIM) a id ITCs (SFN and PEITC) provide chemopreventative activity.

Applicants have recognized that there is a need in the art to understand the mechanism by which indoles and ITCs provide chemopreventative activity and inhibit tumorigenesis, and whether an epigenetic mechanism might be involved. Applicants have recognized that understanding such mechanisms may aid in defining methods of treating or preventing cancer by administering such compounds. The present invention addresses these needs, among others.

SUMMARY OF THE INVENTION

This invention is based, at least in part, on an unexpected discovery that phytochemical compositions participate in demethylation and induction of Nrf2, which in turn upregulates expression of anti-oxidative stress enzymes.

Accordingly, one aspect of this invention features a method for inducing expression of anti-oxidative stress enzymes in a subject in need thereof. The method includes the step of administering to a subject a therapeutically effective amount of a demethylating agent comprising a phytochemical that induces the expression of Nrf2 and Nrf2-mediated genes expressing anti-oxidative stress enzymes. In one embodiment, the subject has a disease or disorder characterized by decreased expression of anti-oxidative stress enzymes. Examples of such anti-oxidzative stress enzymes can include GST, NQO1, SOD1, and HO-1, Examples of oxidative stress disorders include cancer, diabetes, multiple sclerosis, amyotrophic lateral sclerosis. Parkinson's disease, Alzheimer's disease, atherosclerosis, heart failure, myocardial infarction, Schizophrenia, Bipolar disorder, fragile X syndrome, Sickle Cell Disease, and chronic fatigue syndrome. Examples of cancer include breast cancer, colorectal cancer, prostate cancer, and lung cancer. In one embodiment, the demethylating agent is a phytochemical including one or more indoles and isothiocyanates. Examples of such isothiocyanates are phenethyl isothiocyanate (PEITC) and sulfurophane (SFN). Examples of such indoles include 3,3'-diiondolylmethane (DIM) and indole-3-barinol (I3C). The therapeutically effective amount of the demethylating agent of the above-mentioned method can be in the range of from about 1.62 mg/kg to about 3.42 mg/kg per day.

In another, this invention features a method of inhibiting cancer development in a subject. The method includes the step of administering to the subject a therapeutically effective amount of a demethylating agent comprising a phytochemical, wherein the phytochemical is present in an amount effective to induce the expression of Nrf2 and Nrf2-mediated genes expressing anti-oxidative stress enzymes. Examples of such anti-oxidzative stress enzymes can include GST, NQO1, SOD1, and HO-1. Examples of cancer include breast cancer, colorectal cancer, prostate cancer, and lung cancer, in one embodiment, the demethylating agent is a phytochemical including one or more indoles and isothiocyanates. Examples of such isothiocyanates are phenethyl isothiocyanate (PEITC) and sulfurophane (SFN). Examples of such indoles include 3,3'-diiondolylmethane (DIM) and indole-3-barinol (I3C). The therapeutically effective amount of the demethylating agent of the above-mentioned method can be in the range of from about 1.62 mg/kg to about 3.42 mg/kg per day.

In another aspect, this invention features a pharmaceutical composition which includes a demethylating agent and a pharmaceutically acceptable carrier. Preferably, the demethylating agent includes phytochemicals such as indoles and isothiocyanates. In certain embodiments, the indoles include DIM and I3C, and the isothiocyanates include PEITC and SFN. In certain embodiments, the demethylating agent is a pharmaceutically acceptable salt, stereoisomer, tautomer, solvate, or prodrug thereof.

In another aspect, the present invention features a method of inducing Nrf2 activity which includes providing a tissue of interest and contacting the tissue with a demethylating agent as described above.

In another aspect, the present invention features a method of treating a disease or condition selected from proliferative diseases or disorders, metabolic diseases or disorders, cardiovascular diseases or disorders, and neurological diseases and disorders. Such methods include administering, to a subject in need of treatment a therapeutically effective amount of a demethylating agent as described above, in certain embodiments, the disease or disorder can be inflammation, cancer, diabetes, multiple sclerosis, amyotrophic lateral sclerosis, Parkinson's disease, Alzheimer's disease, atherosclerosis, heart failure, myocardial infarction, Schizophrenia, Bipolar disorder, fragile X syndrome. Sickle Cell Disease, and chronic fatigue syndrome.

BRIEF DESCRIPTION OF THE FIGURES

FIG. 1 illustrates the chemical structures of indole-3-carbinol (I3C), 3,3'-indolylmethane (DINT), phenethyl isothiocyanate (PEITC), and sulforaphane (SFN).

FIG. 2 illustrates a schematic diagram of the proposed simplified pathway shows indole and isothiocyanate phytochemicals inducing Nrf2-ARE signaling through activation of the ARE and producing antioxidative and phase II detoxifying genes.

FIG. 3 illustrates Luciferase activity in HepG2-C8 cells. All combinations are described in Example 1 below, 's' denotes synergistic, '#' denotes antagonistic; 'a' denotes additive, though DIM6.25/PEITC1 is considered additive as the combination index (CI) is around 1. The broken lines break the relatively higher fold changes into two corresponding connecting bars; the relative folds across all groups are maintained.

FIGS. 4A-F illustrate real-time PCR (qPCR) results expressed in fold changes of mRNA over the control, using GAPDH as endogenous housekeeping gene; FIG. 4A illustrates Relative expression level of Nrf2 in RNA; FIG. 4B illustrates Relative expression level of HO-1 mRNA. FIG. 4C illustrates relative expression level of NQO1 mRNA; FIG. 4D illustrates relative expression level of SOD1 mRNA. FIG. 4E illustrates relative expression level of UGT1A1 mRNA; FIG.

4F illustrates relative expression level of GSTm2 mRNA. Results are expressed as mean±SEM. The tested concentrations were in μM. *p<0.05, compared with the 0.1% DMSO-treated control cells.

Figure 5:
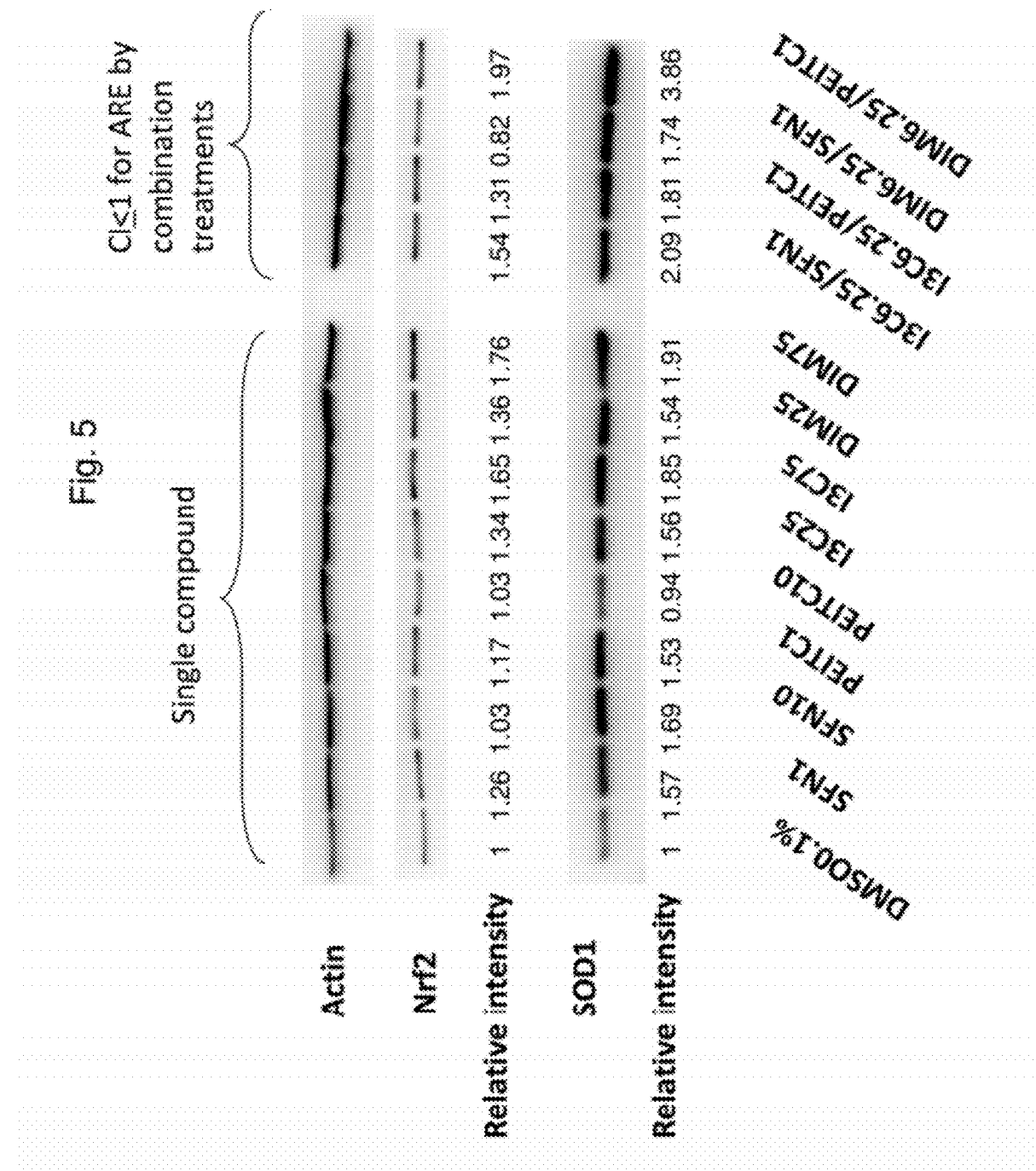

FIG. 5 illustrates Effects of SFN, PEITC, I3C, DIM and their combinations on Nrf2 and SOD1 protein expression in HepG2-C8 cells by western blotting using actin as housekeeping protein. The tested concentrations were in μM. Representative images of three independent experiments are shown.

Figure 6:
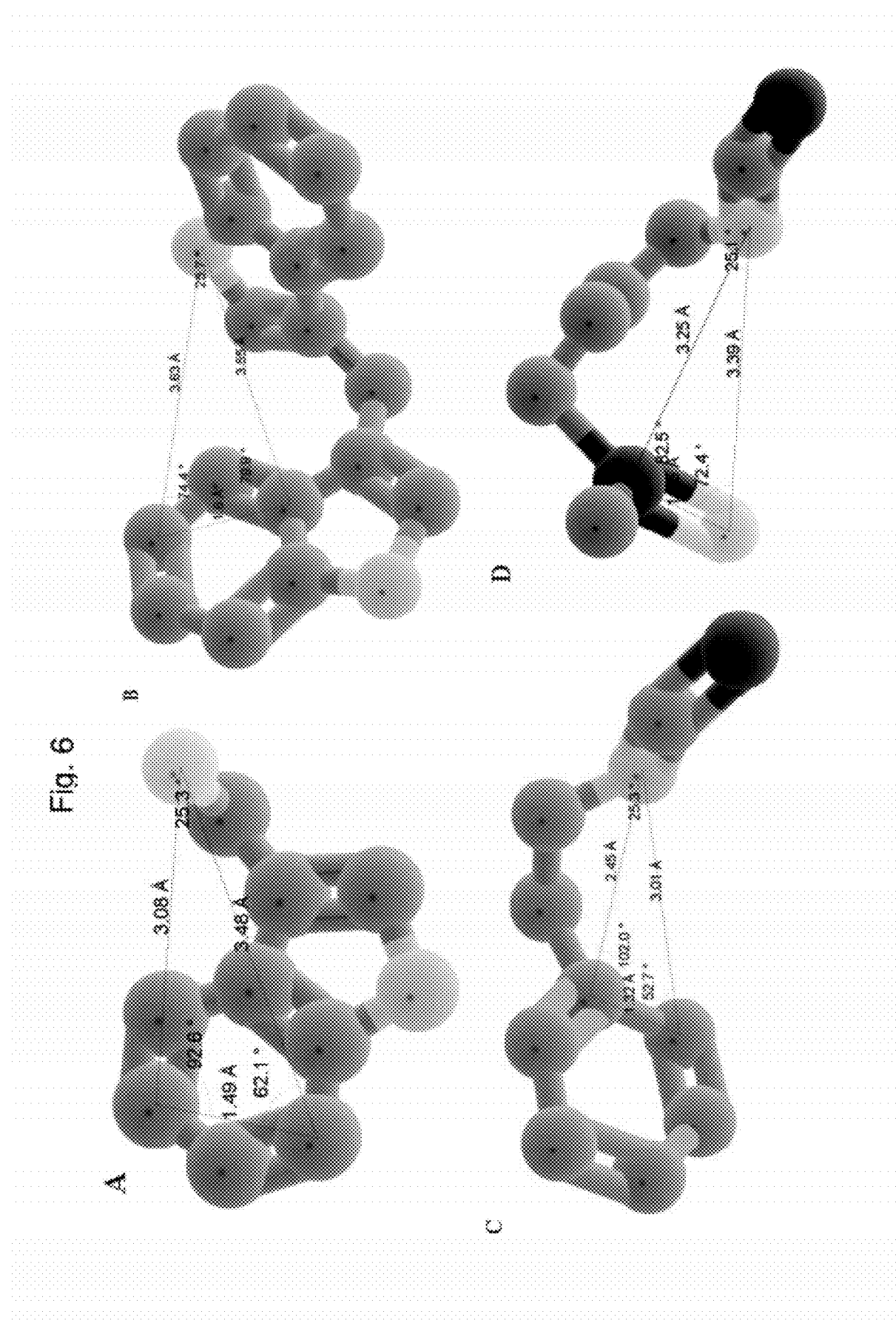

FIGS. 6A-D illustrate the comparison of the structures, the orientations of the structures are shown to illustrate the high degree of overlapping between the structures studied, and also the common pharma-cophore identified, with three atoms brining a pharmacophoric triangle and an angle that is very close to each other; FIG. 6A illustrates I3C, bond angle of 25.3° at $C_2$—$O_{11}$—$C_{10}$; FIG. 6B illustrates DIM, bond angle of 25.7° at $C_2$—$N_{12}$—$C_{19}$; FIG. 6C illustrates PEITC, bond angle of 25.3° at $C_7$—$N_2$—$C_8$; FIG. 6D illustrates SFN, bond angle of 25.1° at $S_4$—$N_1$—$O_5$.

Figure 7:
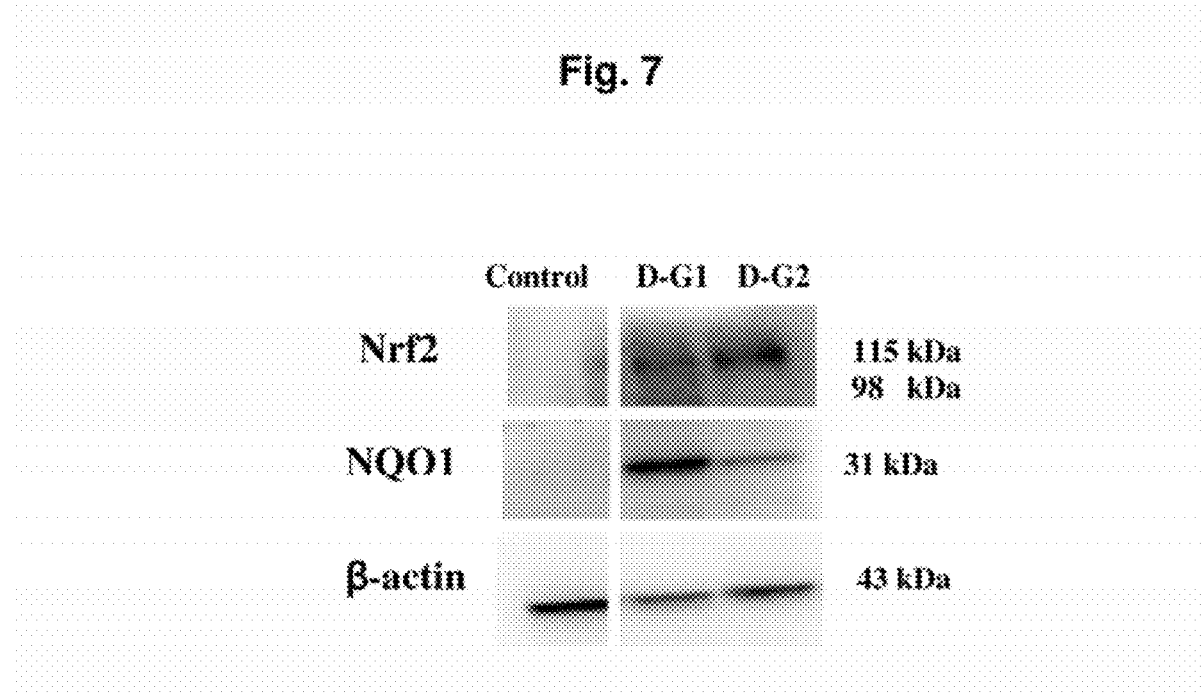

FIG. 7 illustrates Western blots of biomarkers for Nrf2 and Nrf2-regulated NQO1; Nrf2 and NQO1 were re-activated by DIM in D-G1 and D-G2 significantly different from the control.

Figure 8A:
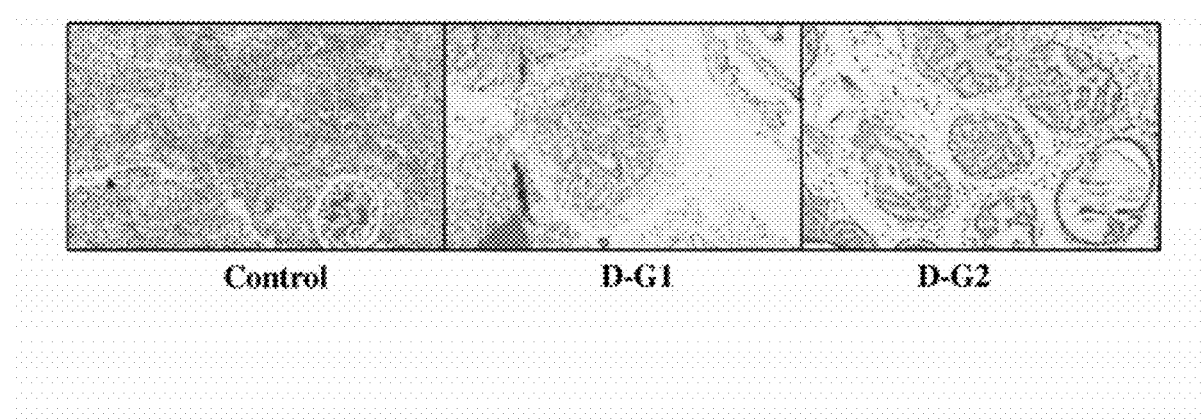

FIGS. 8A-B illustrate de-methylation effects of DIM supplemented diet on TRAMP mice. FIG. 8A illustrates immunohistochemical analysis on the methylation marker, 5-methylcytosin; representative photomicrographs (×40 magnification) of 5-MC stained TRAMP prostate tissue section and percentage levels of methylation; * significantly different from the control (p<0.05) by Mann-Whitne; # significantly different between D-G1 and D-G2. FIG. 8B illustrates the methylation patterns of the first 5 CpGs of promoter Nrf2 gene in TRAMP prostate tissues, and tumors was performed using bisulfit genomic sequencing (BUS); black dots indicate methylated CpGs and open circles indicate un-methylated CpGs; the 5 CpGs were hypermethylated in control group (98% methylation) and either D-G1 or ID-G2 was found significantly to reduce the methylation of the 5 CpGs (37.6%, 54.4%, respectively, Fisher's exact test p<0.001).

Figure 9B:
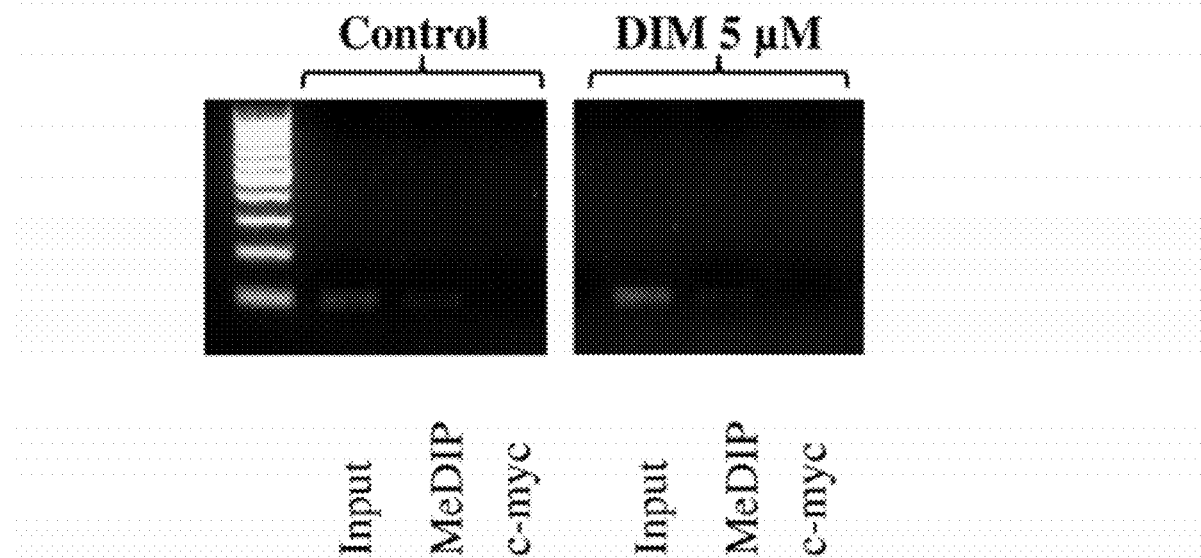
Figure 9C:
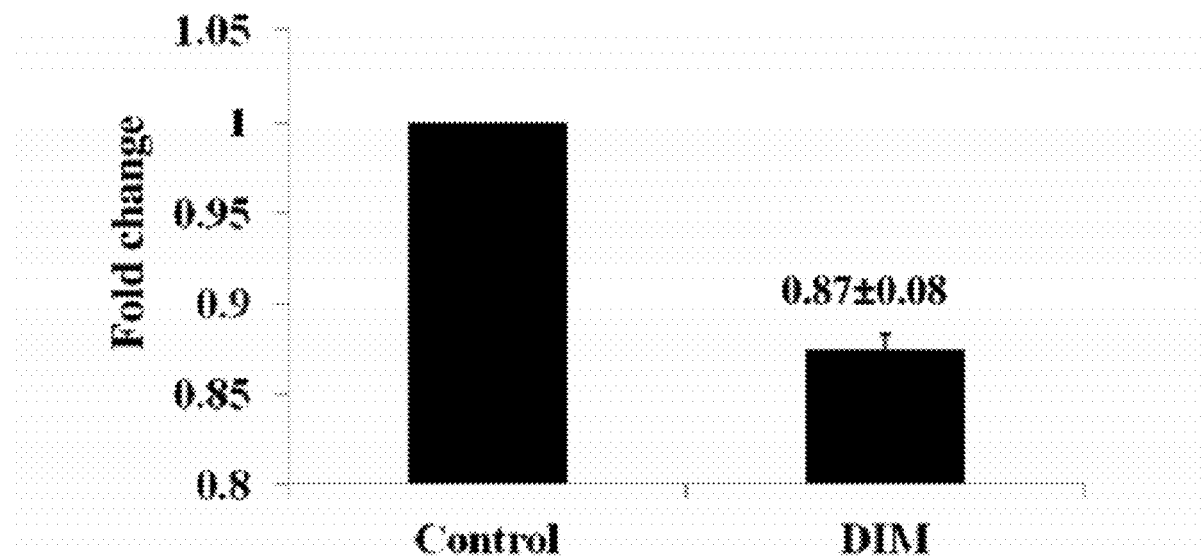

FIGS. 9A-B illustrate de-methylation effects of DIM treated on TRAMP C1 cells. FIG. 9A illustrates the methylation patterns of the first 5 CpGs of promoter Nrf2 gene in TRAMP C1 cells was performed using bisulfit genomic sequencing (BGS); block dots indicate methylated. CpGs and open circles indicate un-methylated CpGs; the 5 CpGs were hypermethylated in TRAMP C1 cells which were untreated control (96.8% methylated); cells treated with either 2.5 μM or 5 μM of DIM for 5 days, the methylation status of these 5 CpGs was reversed significantly (73.7% and 55.8% methylation, respectively, Fisher's exact test, p<0.001); Methylation status of TRAMP C cells treated with DIM 5 μM was significantly lower than DIM 2.5 μM (Fisher's exact test, p=0.015). FIGS. 9B and 9C illustrate that DIM reduced the methylated DNA hound by anti-mecyt antibody to the first 5 CpGs of Nrf2 gene promoter. FIG. 9B shows methylated DNA immunoprecipitation (MeDIP) analysis; semi-quantative PCR was performed to compare the immunoprecipitated DNA with their inputs and negative control (c-myc). FIG. 9C shows bands (MeDIP) that were visualized and quantified using Gel Documentation 2000 system (Bio-Rad, Hercules, Calif.); bars represent mean fold change±SD (normalized with inputs and compared to control value).

FIGS. 10A-B illustrates Nrf2 and Nrf2-mediated genes restored by DIM; FIG. 10A illustrates that mRNA expression levels in DIM treated TRAMP C1 cells; FIG. 10B illustrates Western blots of Nrf2 and NQO1 expression in TRAMP C1 cells. * significantly different from the control (p<0.05) by student's i-test.

FIG. 11 illustrates the effect of the compounds tested on the cell viability determined by MTS assay, using medium with 1% FBS. Results are expressed as the mean±SEM. *p<0.05, compared with corresponding value for 0.1% DMSO-treated cells.

Figure 12A:
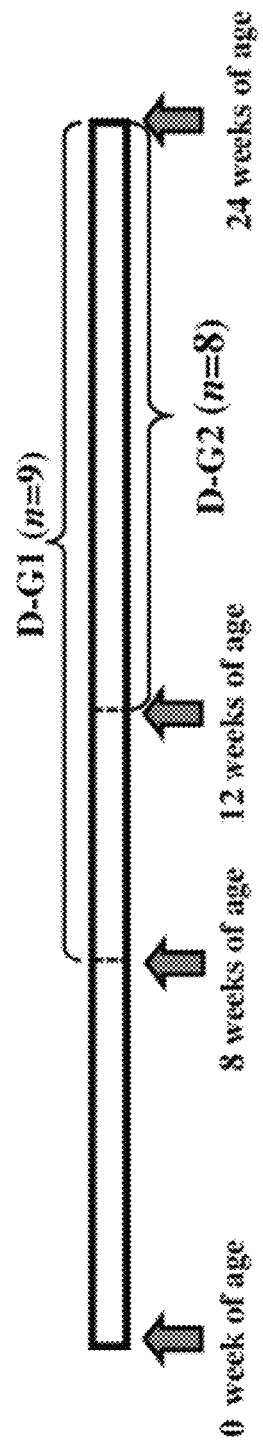
Figure 12B:
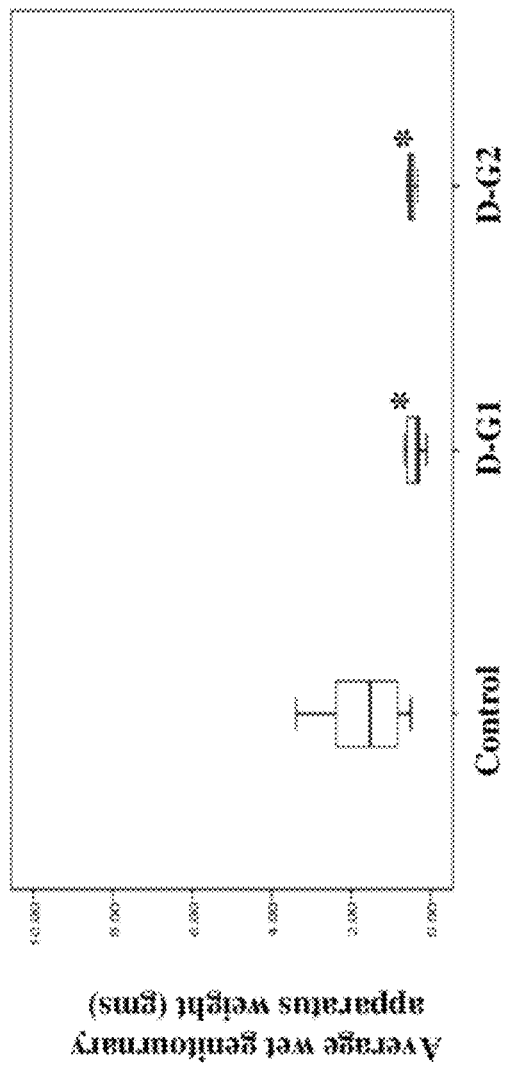
Figure 12C:
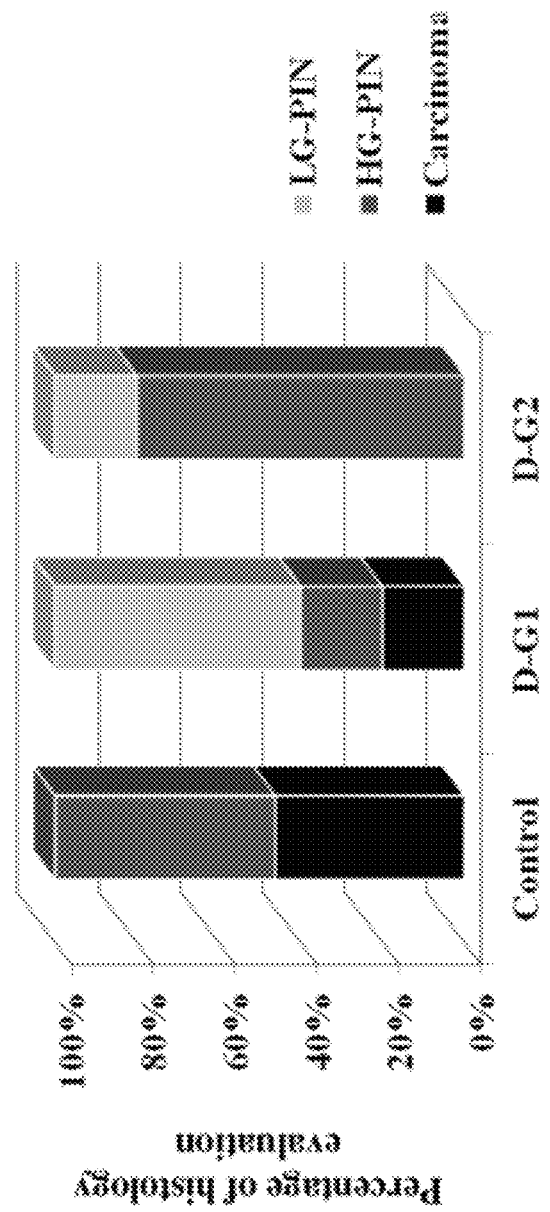

FIGS. 12A-C illustrate the effects of DIM supplemented diet in TRAMP mice; FIG. 12A illustrates the following time lines; D-G1=eight weeks of age TRAMP males were put on AIN-76A diet supplemented with 1% DIM and were sacrificed at 24 weeks of age; D-G2=12 weeks old TRAMP males were put on AIN-76A with 1% DIM and were sacrificed at 24 weeks of age; FIG. 12B illustrates effects of DIM on the genitourinary apparatus weights of animals treated from 8 weeks old and 12 weeks old; * significantly different from the control (p<0.05) based on Mann-Whitney Test; FIG. 12C illustrates histological evaluation of the incidence of PIN and carcinoma. Control group, carcinoma:HG-PIN=46%:54%; D-G1 group, carcinoma:HG-PIN:LG-PIN=20%:20%160%; D-G2 group, HG-PIN:LG-PIN=80%:20%.

FIGS. 13A-B illustrate Immunohistochemical analysis of the effects of DIM supplemented diet on TRAMP males. FIG. 13A illustrates the effects of cell proliferation. PCNA; representative photomicrographs (×40 magnification) of PCNA stained TRAMP prostate tissue section and percentage levels of cell proliferation; * significantly different from the control (p<0.05) was based on Mann-Whitney Test, FIG. 13B illustrates effects of apoptosis. TUNEL; representative photomicrographs (×40 magnification) of TUNEL stained TRAMP prostate tissue section and percentage levels of apoptosis; * significantly different from the control (p<0.05) by Mann-Whitney Test; # significantly different between D-G1 and D-G2 (p=0.043).

FIGS. 14A-B illustrate DIM suppressed DNMTs and HDACs in TRAMP C1 cells; FIG. 14A illustrates the mRNA expression levels of DNMT1, DNMT3a, and DNMT3b suppressed by DIM in TRAMP C1 cells at the concentrations of 5 μM and 10 μM (p<0.05); FIG. 14B illustrates Western blots of the DNMTs and HDACs proteins level in TRAMP C1 cells treated with DIM; * significantly different from the control (p<0.05) by student's t-test.

DETAILED DESCRIPTION OF THE INVENTION

The present invention provides pharmaceutical compositions and methods for treating disorders characterized by reduced expression of anti-oxidative stress enzymes in a subject. Such compositions and methods are based upon the discovery that certain phytochemicals, including indoles, such as 3,3'-diindolylmethane (DIM) and indole-3-carbinol (I3C) and isothiocyanates, such as phenethyl isothiocyanate (PEITC) and sulforaphane (SFN), activate the expression of certain anti-oxidative stress enzymes by demethylation of the Nrf2 promoter region of Nrf2-mediated genes expressing enzymes.

Accordingly, in one aspect, the present invention provides a method for inducing expression of anti-oxidative stress enzymes in a subject in need thereof. The method includes administering to the subject a therapeutically effective amount of a demethylating agent. The demethylating agent includes a phytochemical that induces expression of Nrf2 and Nrf2-mediated genes expressing anti-oxidative stress. Such phytochemicals include indoles, such as 3,3'-diindolylmethane (DIM) and indole-3-carbinol (I3C), and isothiocyanates, such as phenethyl isothiocyanate (PEITC) and sulforaphane (SFN). The chemical structures of DIM, I3C, PEITC, and SFN are presented in FIG. 1. In certain embodiments, the phytochemical can include DIM alone. In certain other embodiments, the phytochemical includes DIM in combination with I3C. The present invention also provides a method for treating a disorder characterized by decreased expression of anti-oxidative stress enzymes. The present invention further provides a method of inhibiting cancer development.

DEFINITIONS

As used herein, the term "treat" or "treating" refers to reversal, alleviation, relief, improvement or inhibition of the progress of, or prevent the disorder or condition to which such term applies, or one or more symptoms of such disorder or condition. The term "treatment" also includes alleviation, elimination of causation of or prevention of cancer. Besides being useful for human treatment, the inventive compositions and methods disclosed herein are also useful for treatment of mammals, including horses, dogs, cats, rats, mice, sheep, pigs, and the like.

As used herein, the term "inhibiting" is understood to mean preventing, suppressing, retarding, blocking or delaying cancer development, such as, for example, by stimulating, inducing, or triggering apoptosis (i.e., genetically determined cell death) in pre-cancerous cells.

As used herein, the term "cancer development" is understood to mean the initial appears of cancerous cells. The term "cancerous cells" is understood to mean cells which have the property of autonomous proliferation and have invaded adjacent tissues.

As used herein, the term "administration" is understood to mean any of a multitude of possible means of administration commonly used in the art, such as, for example, orally, rectally, nasally, or parenterally, and the like, wherein parenteral administration includes, for example, intravenous, intramuscular, intraperitoneal, intrapleural, intravesicular, intrathecal, subcutaneous, as well as topical administration, in addition, "administration" includes administration via any of a multitude of pharmaceutical composition forms con witty used in the art.

As used herein, the term "subject in need thereof" is understood to include any human or animal subjects who have been diagnosed with a disorder characterized by a reduced expression of anti-oxidative stress enzymes, or who may have a predisposition to develop such a disease, genetic or otherwise. Such disorders include cancer, Parkinson's disease, Alzheimer's disease, atherosclerosis, heart failure, myocardial infarction, Schizophrenia, Bipolar disorder, fragile X syndrome, Sickle Cell Disease, and chronic fatigue syndrome.

The subject is typically a mammal. "Mammal," as that term is used herein, refers to any animal classified as a mammal, including humans, domestic and farm animals, and zoo, sports, or pet animals, such as dogs, horses, cats, cattle, and so forth. Preferably, the mammal is a human.

As used herein, the term "therapeutically effective amount" is understood to mean an amount of a demethylating agent necessary to achieve the desired result of inducing the expression of Nrf2 and Nrf2-mediated genes expressing anti-oxidative stress enzymes. It is also understood that the effective amount will normally be determined by a prescribing physician and that the amount will vary according to the age, weight and response of the individual subject, as well as the severity of the subject's symptoms and the potency of the particular compound being administered. Based upon a normal human weight of 70 kg, the effective amount is in the range of from about 113 mg to about 227 mg per day, preferably in the range of from about 141 mg to about 200 mg per day, and more preferably of from about 156 mg to about 185 mg per day. Preferably, the effective amount is in the range of from about 1.62 mg/kg to about 3.24 mg/kg per day, more preferably in the range from about 2.02 mg/kg to about 2.84 mg/kg per week, and even more preferably in the range of from about 2.22 mg/kg to about 2.64 mg/kg per day. The effective amount may be administered in single or divided doses.

Preferred pharmaceutical compositions include oral compositions, such as, for example, solid forms (e.g., tablets, capsules, powders, pills, or granules) or liquid forms (e.g., syrups, emulsions or suspensions); rectal compositions, such as, for example, suppositories; and parenteral compositions, such as, for example, compositions suitable for injection or infusion.

The phrase "pharmaceutically acceptable" is employed herein to refer to those compounds, materials, compositions, and/or dosage forms which are, within the scope of sound medical judgment, suitable for use in human beings and animals commensurate with a reasonable therapeutic benefit/risk ratio.

As used herein, "pharmaceutically acceptable salts" refer to derivatives of the disclosed compounds wherein the parent compound is modified by making counterpart acid or base salts thereof. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non toxic salts or the quaternary ammonium salts of the parent compound formed, for example, from non toxic inorganic or organic acids. Moreover the term may refer to counter ions of any moiety that is designated in this disclosure in an ionic form.

The novel compounds disclosed herein are also intended to be used in a context of prodrugs. The term "prodrugs," as used herein, includes esters and carbonates of the disclosed compounds formed by reacting one or more hydroxyls of compounds with alkyl, alkoxy or aryl substituted acylating agents employing procedures known to those skilled in the art to generate acetates, pivalates, methylcarbonates, benzoates, and the like.

The term "gene" as used herein refers to a DNA sequence, including but not limited to a DNA sequence that can be transcribed into mRNA which can be translated into polypeptide chains, transcribed into rRNA or tRNA or serve as recognition sites for enzymes and other proteins involved in DNA replication, transcription and regulation. This definition includes various sequence polymorphisms, mutations, and/or sequence variants wherein such alterations do not affect the function of the gene product. The term "gene" is intended to include not only regions encoding gene products but also regulatory regions including, e.g., promoters, termination regions, translational regulatory sequences (such as ribosome binding sites and internal ribosome entry sites), enhancers, silencers, insulators, boundary elements, replication origins, matrix attachment sites, and locus control regions. The term "gene" further includes all introns and other DNA sequences spliced from the mRNA transcript, along with variants resulting from alternative splice sites. The term "gene" includes, but is not limited to, structural genes, immunity genes and secretory (transport) genes.

The term "promoter" as used herein refers to a DNA regulatory region capable of binding RNA polymerase in a cell and initiating transcription of a downstream (3' direction)

coding sequence. The promoter is bound at its 3 terminus by the translation start codon of a coding sequence and extends upstream (5' direction) to include a minimum number of bases or elements necessary to initiate transcription.

The term "demethylating agent" as used herein refers to compounds that can inhibit or reverse methylation, resulting, in the expression of the previously hypermethylated genes. Demethylating agents include, for example, phytochemicals such as indoles and isothiocyanates. Preferably, such indoles include 3,3'-diindolylmethane (DIM) and indole-3-carbinol (I3C). Preferably, such isothiocyanates includes phenethyl isothiocyanate (PEITC) and sulforaphane (SFN).

The term "hypomethylation" as used herein refers to the methylation state corresponding to a decreased presence of 5-methyl cytosine nucleotide at one or a plurality of CpG dinucleotides within a DNA sequence of a test DNA sample, relative to the amount of 5-methyl cytosine nucleotide found at corresponding CpG dinucleotides within a normal control DNA sample.

The term "hypermethylation" as used herein refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

As used herein, the terms "upstream" and "downstream" refer to the position of an element of nucleotide sequence. "Upstream" signifies an element that is more 5' than the reference element. "Downstream" signifies an element that is more 3 than the reference element.

Induction of Nrf2-Mediated Phase II Drug Metabolizing and Antioxidant Genes and Synergism with Isothiocyanates One aspect of this invention features a method for inducing expression of anti-oxidative stress enzymes in a subject in need thereof. The method includes the step of administering to a subject a therapeutically effective amount of a demethylating agent comprising a phytochemical that induces the expression of Nrf2 and Nrf2-mediated genes expressing antioxidative stress enzymes. In one embodiment, the subject has a disorder characterized by decreased expression of anti-oxidative stress enzymes. Examples of such anti-oxidzative stress enzymes can include GST, NQO1, SOD1, and HO-1. Examples of oxidative stress disorders include cancer, diabetes, multiple sclerosis, amyotrophic lateral sclerosis. Parkinson's disease, Alzheimer's disease, atherosclerosis, heart failure, myocardial infarction, Schizophrenia, Bipolar disorder, fragile X syndrome, Sickle cell Disease, and chronic fatigue syndrome. Examples of cancer include breast cancer, colorectal cancer, prostate cancer, and lung cancer. In one embodiment, the demethylating agent is a phytochemical including one or more indoles and isothiocyanates, Examples of such isothiocyanates are phenethyl isothiocyanate (PEITC) and sulfurophane (SFN). Examples of such indoles include 3,3"-diiondolylmethane (DIM) and indole-3-barinol (I3C).

In another aspect, this invention features a method of inducing Nrf2 activity including providing a tissue of interest and contacting the tissue with a compound in accordance with a demethylating agent as described herein to activate expression of Nrf2-mediated genes expressing anti-oxidative stress enzymes. In another aspect, this invention features a method of treating a disease or condition. Examples of such diseases that fall within the scope of this invention include proliferative diseases or disorders, metabolic diseases or disorders, cardiovascular diseases or disorders, and neurological diseases and disorders.

The antioxidant response element (ARE) is a critical regulatory element for the expression of many phase II drug metabolizing and anti-oxidant enzymes, mediated by the transcription factor Nrf2. The Nrf2-ARE signaling pathway plays an important role in may diseases and disorders characterized by methylation of Nrf2 and the decreased expression of anti-oxidative stress enzymes. Such diseases include proliferative diseases or disorders, such as cancer, cardiovascular diseases or disorders, and neurological diseases and disorders.

The mechanism by which the phytochemicals described herein prevent cancer involve the Nrf2-ARE-mediated antioxidative stress signaling pathway. FIG. 2 shows the schematic diagram of the mechanism by which ARE and its downstream targeting enzymes are induced. In one aspect, the present invention is based on the synergistic effects of the indoles and the ITC compounds in the activation of the Nrf2-mediated signaling pathway. Accordingly, the present invention addresses treatment of such diseases based upon the surprising and unexpected discovery of activation and synergism of Nrf2-ARE-mediated transcriptional activity by four common phytochemicals: (1) the indoles indole-3-carbinol (I3C) and (ii) 3,3'-diindolylmethane (DIM); and (2) the isothiocyanates (ITCs) (i) phenethyl isothiocyanate (PEITC) and (ii) sulforaphane (SFN).

As discussed above, the present invention also demonstrates that I3C and DIM are effective cancer chemo-preventive agents. At appropriate combinations with SFN and PEITC, both I3C and DIM function synergistically in terms of activating Nrf2-ARE pathway. In certain preferred embodiments, 1 μM SFN with 25 μM DIM, 1 μM SFN with 6.25 μM I3C, 1 μM PEITC with 6.25 μM DIM and 1 μM PEITC with 6.25 μM I3C showed synergistic effects on the activation of Nrf2-ARE pathway, as is discussed in . . . lore detail in Example 3 below.

Synergism is present for different combinations between the indoles and the ITCs at various concentrations, as shown in FIG. 3. qPCR and western blotting confirmed that the phytochemicals were promoting the induction of Nrf2, phase H DME and antioxidant genes. Since preventing diseases including cancer initiation could be achieved by protecting cells and tissues against oxidative stress-mediated damage, the induction of cellular phase II DME/detoxifying and anti-oxidant enzymes such as UGT, GST, NQO1, SOD1 and HO-1 is an effective mechanism of defense against such damage. The induction of these enzymes is mediated by the Nrf2-ARE signaling pathway. In this context, the present invention quantifies the gene expression of Nrf2, HO-1, SOD1, NQO1, UGT and GSTm2 and the induction of these genes, as shown in FIG. 4. The combination of 6.25 μM DIM plus 1 μM PEITC showed the most robust overall synergistic effect compared with the other treatments. One preferred combination includes 6.25 μM DIM with 1 μM PEITC under the experimental conditions described in the Examples below, since synergistic induction was observed for all the genes studied (except GSTm2) and the fold induction was also relatively higher compared with the single agent treatment and the other combinations tested. In addition. FIG. 5 demonstrates that Nrf2 and SOD1 proteins also showed synergism after 24 h of treatment with 6.5 μM DIM plus 1 μM PEITC.

As shown in FIG. 3. SFN is a stronger inducer than PEITC in ARE-luciferase transcription. However, in contrast, PEITC induced higher mRNA levels of endogenous Nrf2 and Nrf2-mediated genes than SFN (FIG. 4). HepG2 cells treated with purr and SFN have shown different time courses and concentration-dependent apoptosis. Time course studies on the induction of ARE-luciferase activities by SFN and PEITC demonstrate that as early as 6 hours, 1 μM PEITC induced higher ARE activities than 1 μM SFN. The slower inducing effect of SFN correlates SFN reaching its peak induction at 18 hours after treatment. Moreover, there are also differences between SFN and PEITC with respect to treatment time for ARE activities (24 h, FIG. 3), mRNA (6 h, FIG. 4) and protein (24 h, FIG. 5). The kinetic profiles for SFN and PEITC in inducing ARE, Nrf2 and Nrf2-mediated genes are quite different. These findings indicate that, in addition to the Nrf2-ARE mediated signaling pathway, other pathways such as the activation of the mitogen-activated protein kinases (MAPKs) are also involved.

The present invention also relates to the common pharmacophore present in the structures of the disclosed demethylating compounds, e.g., the indoles and the ITCs, since they are all able to induce ARE luciferase activities. The inventors utilized an advanced application called Ballon using an MMFF94-like force fielding in obtaining minimized structures. At least one hydrogen acceptor (HA) is present in the four phytochemicals studied, as show in Table 1 below. This is consistent with HA being one of the critical properties responsible for the ARE inducting activities as a pharmacophore.

as the dose used, specificity of the compound to the binding site, kinetic profiles and extend of metabolism of the compounds also need to be taken into consideration. Taken together, this information provides new information for synthesizing or chemical modifications (in addition to the other different physiochemical properties and acid-base properties to be considered), at least for the indoles and ITCs, for the design of new chemopreventive compounds that induce ARE and enhance the Nrf2-mediated antioxidant and phase II detoxifying gene expression pathway which would yield a higher probability of reducing oxidative stress and prevention of carcinogenesis.

Epigenetic Modifications of Nrf2 CpG Island by 3,3'-Diindolylmethane in TRAMP Prostate Tumors and in TRAMP C1 Cells Nrf2, a key regulator of cellular antioxidant defense system is silenced during the development and progression of prostate tumor in transgenic adenocarcinoma of mouse prostate (TRAMP) mice. In one aspect, the present invention relates the potential epigenetic mechanism of DIM as a DNA demethylation agent which may be involved in preventing prostate tumorigenesis in TRAMP mice and in TRAMP C1 cells. TRAMP mice fed with DIM-supplemented diet show a much

TABLE 1

Physicochemical properties of phytochemicals studied

| Phytochemical | Linear formula | Molecular weight | Molecular volume[a] | PSA[b] | ALogP | H donor | H acceptor |
|---|---|---|---|---|---|---|---|
| I3C | $C_9H_9NO$ | 147.18 | 184.68 | 36.02 | 1.2845 | 2 | 2 |
| DIM | $C_{17}H_{14}N_2$ | 246.31 | 308.12 | 31.58 | 3.6737 | 2 | 2 |
| PEITC | $C_6H_5CH_2CH_2NCS$ | 163.24 | 213.10 | 44.45 | 2.5486 | 0 | 1 |
| SFN | $C_6H_{11}NOS_2$ | 177.29 | 224.82 | 80.73 | 0.1647 | 0 | 2 |

[a] unit in cubic angstrom ($Å^3$)
[b] unit in square angstrom ($Å^2$)
ALogP is atomic-based octanol/water partition coefficient A pharmacophore is a molecular framework that carriers the essential features responsible for a drug's (pharmacon's) biological activity which was first defined by Paul Enrlich 100 years ago and is still currently used widely in medicinal chemistry for drug design. Therefore, the geometric distance was analyzed and a pharmacophoric triangle common in the two different chemical functional groups was identified, i.e., the HA is connecting to the other two sides of the structures and possess a very similar bond angle and pharmacophore group, as shown in Table 2 below and FIG. 5.

lower incidence of tumorigenesis and metastasis than an untreated control group. DIM increased apoptosis, decreases cell proliferation and enhances expression of Nrf2 and the Nrf2-target gene NQO1 in prostate tumor tissues.

Immunohistochemical (IHC) analysis shows that DIM reduced CpG 5-methylcytosine staining globally. Bisulfite genomic sequencing (BGS) shows that DIM treatment decreased the methylation status of the first 5 CpGs of the Nrf2 promoter region. In TRAMP-C1 cells, DIM suppresses DNA methyltransferase (DNMT) expression and reverses

TABLE 2

The common structural properties-pharmacophore groups in phytochemicals studied

| Phytochemical | Distances among the three atoms forming the pharmacophoric triangle (Å) | | | Bond angle of the pharmacophoric triangle (°) | Reference structure |
|---|---|---|---|---|---|
| I3C | $O_{11}$—$C_2$ = 3.08 | $O_{11}$—$C_{10}$ = 3.48 | $C_{10}$—$C_2$ = 1.49 | $C_2$—$O_{11}$—$C_{10}$ = 25.3 | FIG. 6A |
| DIM | $N_{12}$—$C_2$ = 3.63 | $N_{12}$—$C_{19}$ = 3.55 | $C_{19}$—$C_2$ = 1.60 | $C_2$—$N_{12}$—$C_{19}$ = 25.7 | FIG. 6B |
| PEITC | $N_2$—$C_7$ = 2.45 | $N_2$—$C_8$ = 3.01 | $C_8$—$C_7$ = 1.32 | $C_7$—$N_2$—$C_8$ = 25.3 | FIG. 6C |
| SFN | $N_1$—$S_4$ = 3.25 | $N_1$—$O_5$ = 3.39 | $S_4$—$O_5$ = 1.45 | $S_4$—$N_1$—$O_5$ = 25.1 | FIG. 6D |

Note:
the subscript number at an atom denotes the atom number in the respective structure The ALogP value is an index of the hydrophobicity of a compound, in the current study SFN is the least hydrophobic, followed by I3C, DIM and PEITC. Compounds with high hydrophobicity will have greater membrane permeabilities, and will account in part for the in vitro activities observed. In this Nrf2-ARE inducing activities testing, other factors such CpG methylation of Nrf2 resulting in enhanced expression of Nrf2 and Nrf2-target gene. NQO1, as shown in FIG. 7. Accordingly, the present invention relates to the surprising discovery that DIM potently inhibits PCa tumorigenesis, epigenetically modifies the CpG of Nrf2 in vivo and in vitro, and enhances expression of Nrf2 and Nrf2-mediated genes.

TRAMP mice fed with a DIM-supplemented diet have a lower percentage of palpable tumor and incidence of lymph node metastasis as compared to a control diet (5.8% vs. 31.6% for palpable tumor in treated vs. control and 0% vs. 26.3% for lymph node metastasis in treated vs. control), as Shown in Table 3 below.

TABLE 3

DIM inhibit palpable tumor and metastasis in TRAMP males

| | Number of animals | Incidence of palpable tumor | Incidence of lymph nodes metastasis |
|---|---|---|---|
| Control | 19 | 6/19[a] | 5/19[b] |
| DIM_8 wk (D-G1) | 9 | 1/9[a,] | 0/9[b, #] |
| DIM_12 wk (D-G2) | 8 | 0/8[a, *] | 0/8[b, #] |

[a]Numbers represent the presence of palpable tumor showed at the end of the experiment at 24 weeks of age. Fisher's exact test was used to compare the incidence of palpable tumor between the control and the DIM treated mice sacrificed at 24 weeks of age. p values < 0.05 were considered as significant, indicated by *.
[b]Numbers represent the presence of lymph nodes metastasis showed at the end of experiment when the mice were sacrificed. Fisher's exact test was used to compare the incidence of lymph node metastasis between the control and the DIM treated mice sacrificed at 24 weeks of age. p values < 0.05 were considered as significant, indicated by #.

To investigate the anti-cancer chemopreventive effect of DIM in different stages of prostate tumorigenesis, DIM was supplemented in the diet to TRAMP mice starting at 8 weeks of age (D-G1), when the LG-PIN starting to form, and 12 weeks of age (D-G2) when some of the LG-PINs progress into HG-PINs. As discussed in the Examples below, both D-G1 and D-G2 show a significantly lower percentage of genome-wide 5-MC IHC staining in IHC analysis, as demonstrated in FIG. 8A. Accordingly, DIM impacts the global CpG methylation epigenomic profiles.

DIM substantially reduces the methylation status of the first 5 CpGs of the Nrf2 promoter region, as shown in FIGS. 8A and 8B. This leads to increase or re-expression of Nrf2 and Nrf2-target gene NQO1 proteins in vivo, as shown in FIG. 7. In addition, administration of DIM at the early stage of tumorigenesis achieves superior anti-cancer chemoprevention. For example, administration of DIM starting a 8 weeks old when low grade PIN lesions started to form achieves a better anti-cancer chemopreventive effect than if given later at 12 weeks old when some of the LG-PINs have progressed to HG-PINs.

In vitro BGS of TRAMP C1 cells also shows that DIM reduces the methylation status of the first 5 CpGs on the Nrf2 promoter region, as shown in FIG. 9A. MeDIP/ChIP assay also shows that DIM reverses the CpG methylated DNA on the Nrf2 gene promoter region in TRAMP C1 cells, as shown in FIGS. 9B and 9C. The demethylation of the Nrf2 gene is associated with the enhanced mRNA expression of Nrf2 and Nrf2-target genes such as NQO-1, GSTm1, as shown in FIG. 10A, as well as increased protein levels of Nrf2 and NQO-1, as shown in FIG. 10B. Furthermore, the demethylation effects of DIM correlate with DIM's ability to suppress the expression of DNMTs and HDACs. DNMT1 is one of the key maintenance DNMTs, and the most abundance DNMTs in mammalian cells. In human cancer cells, DNMT1 is responsible for both the de novo and the maintenance of promoter CpG islands methylation of tumor suppressor genes. Coincidentally, other DNA de-methylating agents such as curcumin and 5-aza+TSA also show decreased CpG methylation of the first 5 CpGs of the promoter of Nrf2 gene and enhanced the expression of Nrf2 and Nrf2-target genes in TRAMP C1 cells.

The ability of DIM in restoring the expression of Nrf2 and its downstream genes via epigenetic mechanism plays an important role in preventing the development and progression of prostate tumor in TRAMP mice in vivo. Advanced and metastasized cancers in human are resistant to radiation and chemotherapy, and epigenetic changes arise earlier than genetic defects during prostatic carcinogenesis. Accordingly, one aspect of the present invention relates to the clinical use of DIM to prevent, block or delay the progression of benign tumors from becoming advanced/metastasized, cancers through epigenetic modifications.

Pharmaceutical Therapeutics

In another aspect, the present invention provides use of a compound according to any embodiments described herein, or a pharmaceutically acceptable salt, stereoisomer, tautomer, solvate, or prodrug thereof, in the manufacture of a medicament for treating a disease or disorder selected from inflammatory diseases or disorders, proliferative diseases or disorders, metabolic diseases or disorders, cardiovascular diseases or disorders, and neurological diseases and disorders. Such compositions include a demethylating agent including a phytochemical, preferable an indole and/or an isothiocyanate. In certain embodiments, the indoles includes 3,33-indolylmethane and indole-3-carbinol, and the isothiocyanates include isothiocyanate and sulforaphane.

In another aspect, the present invention provides a method of inducing Nrf2 activity comprising: providing a tissue of interest; and contacting said tissue with a compound according to any embodiments described herein or a pharmaceutically acceptable salt, stereoisomer, tautomer, solvate, or prodrug thereof, to activate the antioxidative stress system.

In another aspect, the present invention provides a method of treating a disease or condition selected from proliferative diseases or disorders, metabolic diseases or disorders, cardiovascular diseases or disorders, and neurological diseases and disorders, comprising administering to a subject in need of treatment a therapeutically effective amount of a compound according to any embodiments described herein, or a pharmaceutically acceptable salt, stereoisomer, tautomer, solvate, or prodrug thereof.

The disease or disorder is one selected from cancer, diabetes, multiple sclerosis, amyotrophic lateral sclerosis Parkinson's disease, Alzheimer's disease, atherosclerosis, heart failure, myocardial infarction, Schizophrenia. Bipolar disorder, fragile X syndrome, Sickle Cell Disease, and chronic fatigue syndrome. Examples of cancer include breast cancer, colorectal cancer, prostate cancer, and lung cancer.

Pharmaceutical formulations of the present invention include those suitable for oral, nasal, topical (including buccal and sublingual), rectal, vaginal and/or parenteral administration. Regardless of the route of administration selected, the active ingredient(s) are formulated into pharmaceutically acceptable dosage forms by methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly mixing the active ingredient(s) into liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredient(s). The active ingredient(s) may also be administered, as a bolus, electuary or paste.

In solid dosage forms of the invention for oral administration capsules, tablets, pills, dragees, powders, granules and the like), the prodrug(s), active ingredient(s) (in their micronized form) is/are mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering, agents. Solid compositions of a similar type may also be employed, as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient(s) moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient(s) therein using, for hydroxypropyl-methyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient(s) can also be in microencapsulated form.

Liquid dosage forms for oral administration of the active ingredient(s) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethylacetate, butyl alcohol, benzyl benzoate, propylene glycol, glycol, oils (in particular, cottonseed groundnut, corn, germ, olive, castor and sesame oils), glycerol, amyl alcohol, tetrahydrofuryl polyethylene glycols and fatty acid esters of sorbitan, and mixtures thereof.

Besides inert diluents the oral compositions can also include adjuvants such as wetting agents, emulsifying and suspending agents, sweetening, flavoring, coloring, perfuming and preservative agents. Suspensions, in addition to the active ingredient(s), may contain suspending agents as, for example, ethoxylated alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the active ingredient(s) with one or more suitable nonirritating excipients or carriers comprising, for example, cocoa butter, polyethylene glycol, wax and which is solid at room temperature, but liquid at body temperature and, therefore, will melt in the rectum or vaginal cavity and release the active ingredient(s). Formulations of the present invention which are suitable for vaginal administration also include pessaries, tampons, (Teams, gels, pastes, foams or spray formulations containing such carriers as are known in the art to be appropriate.

Dosage forms for the topical or transdermal administration of the active ingredient(s) include powders sprays, ointments, pastes, creams, lotions, gels, solutions, patches and inhalants. The active ingredient(s) may be mixed under sterile conditions with pharmaceutically-acceptable carrier, and with any buffers, or propellants which may be required.

The ointments, pastes, creams and gels may contain, in addition to the active ingredient(s), excipients, such as animal and Vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient(s), excipients such as lactose, talc, silicic acid, aluminum hydroxide, calcium silicates and polyamide powder, or mixtures of these substances. Sprays can additionally contain customary propellants such as chlorofluoro-hydrocarbons and volatile unsubstituted hydrocarbons, such as butane and propane.

Compounds of the present invention may be administered in intranasal form via topical use of suitable intranasal vehicles, or via transdermal routes, using those forms of transdermal skin patches well known to those of ordinary skill in the art. A transdermal delivery system provides for continuous administration throughout the dosage regimen. Transdermal patches have the added advantage of providing controlled delivery of the active ingredient(s) to the body. Such dosage forms can be made by dissolving, dispersing or otherwise incorporating the active ingredient(s) in a proper medium, such as an elastomeric matrix material. Absorption enhancers can also be used to increase the flux of the active ingredient(s) across the skin. The rate of such flux can be controlled by either providing a rate-controlling membrane or dispersing the active ingredient(s) in a polymer matrix or gel.

The compounds of the present invention can also be administered in the form of liposome delivery systems, such as small unilamellar vesicles, large unilamellar vesicles and multi lamellar vesicles. Liposomes can be formed from a variety of phospholipids, such as cholesterol, stearylamine or phosphatidylcholines.

Another mode of delivery for the compounds of the present invention may be delivery via the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, poly epsilon caprolactone polyhydroxy butyric acid, polyorthoesters, polyacetals, polydihydropyrans, polycyanoacrylates and crosslinked or amphipathic block copolymers of hydrogels.

Pharmaceutical compositions of this invention suitable for parenteral administration comprise the active ingredient(s) in combination with one or more pharmaceutically-acceptable sterile isotonic aqueous or nonaqueous solutions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its their rate of dissolution which, in turn, may depend upon crystal size and crystalline form.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly(orthoesters) and poly(anhydrides). Depot injectable formulations are also prepared by entrapping the active ingredient(s) in liposomes or microemulsions which are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions maybe prepared from sterile powders, granules and tablets of the type described above.

The following examples are provided to further illustrate the methods and compositions of the present invention. These examples are illustrative only and are not intended to limit the scope of the invention in any way.

EXAMPLES

Example 1

Methods and Materials

This example describes general methods and materials used in Examples 2-6,

A. Materials

The I3C, DIM and PEITC were purchased from Sigma Chemicals Co. (St Louis, USA). The SFN was obtained from LKT Laboratories (St Paul, USA).

B. Cell Culture

The stably transfected single clone HepG2-ARE-C8 (HepG2-C8) cell line has been established previously in our laboratory using the pARETI-luciferase reporter gene. The cells were maintained in Dulbecco's modified Eagle medium supplemented with 10% fetal bovine serum (FBS), 1.17 g/l sodium bicarbonate, and 100 unit/ml penicillin, 100 μg/ml streptomycin at 37° C. in a humidified incubator with 5% $CO_2$.

C. MTS Assay

The cytotoxicity of the phytochemicals was tested in HepG2-C8 cells using the CellTiter 96 aqueous non-radioactive cell proliferation MTS assay [3-(4,5-dimethylthiazol-2-yl)-5-(3-carboxymethoxyphenyl)-2-(4-sulfophenyl)-2Htetrazolium, inner salt; MTS] (Promega, Madison, Wis.). The cells were first cultured in 96-well plates for 24 h and then were treated with I3C, DIM, PEITC or SFN at various concentrations for 2.4 μl. The cells were then treated with MTS for 1 h at 37° C. Absorbance of the formazan product was read at 490 nm with a μQuant Biomolecular Spectrophotometer from Bio-Tek Instruments Inc. (Winooski, Vt.). Independent control studies were conducted using 1% and 10% FBS medium.

D. ARE-Luciferase Assay

The HepG2-C8 cells were cultured in 12-well plates and each well contained 1 million cells in 1 ml of 10% FRS medium. The cells were treated with compounds for 24 h. The luciferase activity was determined using a luciferase kit from Promega (Madison, USA) according to the manufacturer's instructions. Briefly, after treatments for 24 h, the cells were washed twice with ice-cold phosphate buffered-saline (PBS, pH 7.4) and harvested in 1× reporter lysis buffer and kept at overnight. After centrifugation at 4° C., 12000 rpm for 5 min, a 10 μl aliquot of the supernatant was assayed for luciferase activity with a Sirius luminometer (Berthold Detection System GmbH, Pforzheim, Germany). The luciferase activity was normalized against protein concentration, determined by a BCA protein assay (Pierce, Rockford, USA), and expressed as the fold induction over the luciferase activity of control vehicle-treated cells. At least two to three independent studies were conducted in triplicates.

E. RNA Extraction and Quantitative Real-Time PCR

The cells were treated similarly to the NITS and ARE-luciferase assays described above using 10% FBS medium. The incubation of the compounds with the cells was terminated 6 h later. The mRNA expression was evaluated utilizing a quantitative real-time polymerase chain reaction (qPCR). An RNeasy kit from Qiagen was used for RNA extraction (Valencia, Calif.). The total RNA was reverse-transcribed to cDNA by TaqMan Reverse Transcription Reagents (Applied Biosystems Inc, Foster City, Calif.). SYBR Green (Applied Biosystems Inc, Foster City, Calif.) fluorescence was used to measure the product of qPCR. Glyceraldehyde 3-phosphate dehydrogenase (GAPDH) was used as the housekeeping gene, and the Applied Biosystems 7900HT Fast Real-Time PCR System (Applied Biosystems Inc, Foster City, Calif.) was used as described previously (Saw et al., *Biochem Pharmacol* 2010; 79: 421-430) to detect quantitatively the induction of mRNA of Nrf2, phase II DME GSTm2, NAD (P)H dehydrogenase, quinone 1 (NQO1), UGT family, polypeptide A1 (UGT1A1) and antioxidant enzymes HO-1, superoxide dismutase 1 (SOD1). The primer pairs were designed using the Primer Quest Oligo Design and Analysis Tool by Integrated DNA Technologies Inc. (Coralville, Iowa, USA) and the sequences are listed in Table 4. At least four wells of each treatment were performed and duplicate samples were carried out for each treatment.

USA) and denatured at 95° C., for 5 min. The samples and the protein standard (Bin-Rad, Hercules, Calif., USA) were then loaded onto a polyacrylamide gel (Criterion Tris-HCl gel, Bio-Rad Lab, Hercules, Calif., USA) and gel electrophoresis was run at 130 mA for 60 min. Proteins were transferred onto a polyvinylidene difluoride (PVDF) membrane (Immobilon-P, Millipore, Bedford, Mass., USA) over 1.5 h using: a semi-dry transfer system (BioRad, Hercules, Calif., USA). The membranes were blocked with 5% bovine serum albumin (BSA) solution for 1 h at room temperature and incubated with the primary antibody (1:1000, in 3% BSA in Tris-bufferedsaline and Tween 20, TBST) overnight at 4'T. Antibody against actin (catalog no. sc-1616) and SOD1 (catalog no. sc-11407) were purchased from Santa Cruz (Santa Cruz Biotechnology, Inc., CA, USA). Antibody against Nrf2 (catalog no. 2178-1) was purchased from Epitomics (Burlingame, Calif., USA). After hybridization with primary antibody, the membranes were washed with TBST four times. The immunoreactions were continued with the respective secondary antibodies (1:5000, in 3% BSA in TBST) purchased from Santa Cruz Biotechnology, Inc., CA, USA, for 1 h at room temperature. After washing four times with TBST, the immunocomplexes were determined using the enhanced chemiluminescent system to detect horseradish peroxidase on the immunoblots (Thermo Scientific, Rockford, Ill. USA) and

TABLE 4

Human oligonucleotide primers used for qPCR

| Gene | Association no. | Forward (5') primer | Reverse (3') primer |
|---|---|---|---|
| Glyceraldehyde 3-phosphate dehydrogenase (GAPDH) | NM_002046.3 | 5'-TCG ACA GTC AGC CGC ATC TTC TTT-3' (SEQ ID NO: 1) | 5'-ACC AAA TCC GTT GAC TCC GAC CTT-3' (SEQ ID NO: 2) |
| Glutathione S-transferase mu 2 (GSTm2) | NM_000848 | 5'-ACT AAA GCC AGC CTG ACC TTC CTT-3' (SEQ ID NO: 3) | 5'-AAT GCT GCT CCT TCA TGC AAC ACG-3' (SEQ ID NO: 4) |
| Hemeoxygenase-1 (HO-1) | NM_206866 | 5'-ACG CGT TGT AAT TAA GCC TCG CAC-3' (SEQ ID NO: 5) | 5'-TTC CGC TGG TCA TTA AGG CTG AGT-3' (SEQ ID NO: 6) |
| NAD(P)H dehydrogenase, quinone 1 (NQO1) | NM_001025434 | 5'-AAG GAT GGA AGA AAC GCC TGG AGA-3' (SEQ ID NO: 7) | 5'-GGC CCA CAG AAA GGC CAA ATT TCT-3' (SEQ ID NO: 8) |
| Nuclear factor (erythroid-derived 2)-like 2 (Nrf2) | NM_001145413 | 5'-TGC TTT ATA GCG TGC AAA CCT CGC-3' (SEQ ID NO: 9) | 5'-ATC CAT GTC CCT TGA CAG CAC AGA-3' (SEQ ID NO: 10) |
| Superoxide dismutase 1 (SOD1) | NM_000454 | 5'-GCA CCC CAT CAT CAA TTT CGA GCA-3' (SEQ ID NO: 11) | 5'-TGC AGG CCT TCA CTC AGT CCT TTA-3' (SEQ ID NO: 12) |
| UDP-Glucuronosyltransferase 1 family, polypeptide A1 (UGT1A1) | NM_000463 | 5'-ATG ACC CGT GCC TTT ATC ACC CAT-3' (SEQ ID NO: 13) | 5'-AGT CTC CAT GCG CTT TGC ATT GTC-3' (SEQ ID NO: 14) |

F. Western Blotting

The cells were treated similarly to the MTS. AREluciferase and qPCR assays described above, using 10% FBS medium. The HepG2-C8 cells were treated with the compound for 24 h. The cells were washed with ice-cold PBS (pH 7.4) and harvested in cell culture lysis reagent (Promega E153A, Madison, Wis.). The homogenate was centrifuged at 4° C., 12000 rpm for 5 min. The supernatants were collected and 15 µg of total protein, as determined by BCA protein assay (Pierce, Rockford, USA), was mixed with 5 µl Laemmli's SDS-sample butler (Boston Bioproducts, Ashland, Mass., the bands were visualized and captured by a BioRad ChemiDoc XRS system (Hercules, Calif., USA).

G. Combination Index Calculation

To determine the synergistic effect between the combination of two different compounds, the combination index (CI) was calculated with the following formula: $CI = d1/Dx,1 + d2/Dx,2$ where d1 and d2 are doses of drugs 1 and 2 in combination, which produces an effect x. $Dx,1$ and $Dx,2$ are the doses of drug 1 and 2 that produce the same effect x when given alone. When the CI is equal to, less than or greater than 1, the combination dose will be additive, synergistic or antagonistic, respectively, as described previously. This approach is based on the Loewe additivity model and although the exact mechanism of interaction may be unknown, this model is one of the most commonly used reference models for evaluating potential drug-drug interactions Lee et al., *J Biopharm Stat* 2007; 17: 461-480). Using this CI calculation for the ARE-luciferase activity induced by I3C or DIM combined with PEITC or SFN, it is possible to identify whether the combination of these phytochemicals at certain concentrations would be synergistic, antagonistic or additive.

Computational Analysis

To elucidate the potential pharmacophore group that would contribute to Nrf2/ARE activation, the structural properties of the 4 compounds were operated using Symyx® Draw 3.2 (Symyx Solutions Inc., Sunnyvale, Calif.) and the structures were subject to energy minimization by Ballon version 1.0.1.484. The geometrical analysis to identify common pharmacophore group was performed using Jmol.

I. Statistical Analysis

The results are presented as mean±standard error of the mean (SEM). MTS assay data were analyzed using one-way ANOVA with a post hoc multiple comparison analysis by Bonferroni. Luciferase assay and qPCR data were analyzed statistically using Students t test. Values of $p<0.05$ were considered to be statistically significant.

Example 2

Cell Viability by MTS Assay

To test the cell viability of I3C, DIM, SFN and PEITC, the MTS assay was employed, DIM and I3C showed less toxicity than SFN and PETIT in 1% FIBS medium (FIG. 11), SFN and PEITC showed similar cell viability inhibitory concentrations (IC50) of around 20 µM, whereas I3C and DIM had a higher IC50 of 135 µM and 51 µM, respectively. Using 10% FBS, several previous publications showed that DIM was more cytotoxic than I3C, hence the same dosage was tested in HepG2-C8 cells with 10% FBS. The cytotoxicity of HepG2-C8 was affected more with DIM than I3C, e. DIM showed an IC50 of around 85 µM, while I3C showed an IC50 of 300 µM in 10% FBS medium (data not shown).

Example 3

ARE-Luciferase Activity

In the ARE transcriptional activation assay, the cells were treated with higher doses of DIM and I3C (25 and 75 µM), since from the MTS assay the viability was not affected at these concentrations in 1.0% FBS medium (data not shown). To evaluate the transcriptional activation of ARE, an ARE-luciferase reporter assay was performed. SFN and PEITC were used as positive controls and 0.1% DMSO was used as a negative control. The ARE-luciferase activity was expressed as the fold induction over the negative vehicle control. All compounds alone and in combinations induced ARE-luciferase activity in HepG2-C8 cells with different potency, as shown in FIG. 3. DIM at 75 µM strongly induced the ARE-luciferase compared with any other treatment ($p<0.05$). 25 µM DIM with 1 µM SFN (DIM25/SFN1) was synergistic but not for 25 µM I3C with 1 µM SFN, as shown in FIG. 3. Although there were three synergistic interactions at low doses of combination having ARE activities close to value 1, all the CI were <1, and $p<0.05$. Specifically, synergistic effects were observed for the combinations of 6.25 µM I3C with 1 µM SFN (I3C6.25/SFN1, p value for CI=0.045), 6.25 µM I3C with 1 µM PEITC (I3C6.25/PEITC1, p value for CI=0.044) and 6.25 µM DIM with 1 µM PEITC (DIM6.25/PEITC1, p value for CI=0.003). An additive effect was observed with 6.25 µM DIM with 1 µM SFN (DIM6.25/SFN1), whereas 25 µM I3C with 1 µM SFN (I3C25/SFN1) was antagonistic. The DIM25/SFN1 treatment displayed the most synergism, and I3C6.25/SFN1, DIM6.25/PEITC1 and I3C6.25/PEITC1 were not so obvious, however, their CI values were less than 1 synergistic), DIM6.25/SFN1 had a CI value of 1 (i.e., additive). I3C2.5/SFN1 had a CI value of more than 1 (i.e., antagonistic). The classification of synergistic, additive or antagonistic was based mathematically on the CI calculations that were derived from the dose response of a single compound, and the response of the combinations at different doses. The effects of using a different cell density at similar drug concentrations in medium with 1% FBS gave similar observations (data not shown). When doses of I3C and DIM lower than 25 µM were tested in 10% FBS medium, no significant induction was observed (data not shown). As there was an obvious dose response for single treatment with DIM (i.e., DIM25 and DIM75), and not for I3C25 and I3C75, however, the CI calculations for DIM25/SFN1 and I3C25/SFN1 showed CI of 0.7 and 3, respectively. Next, the study verified the identified additive/synergistic combinations, particularly at those lower concentrations that may be more physiologically relevant concentrations of indoles and ITCs using quantitative real-time polymerase chain reaction (qPCR) and western blotting analyses for the Nrf2-ARE-mediated genes, as described below.

Example 4 qPCR

Figure 4B:
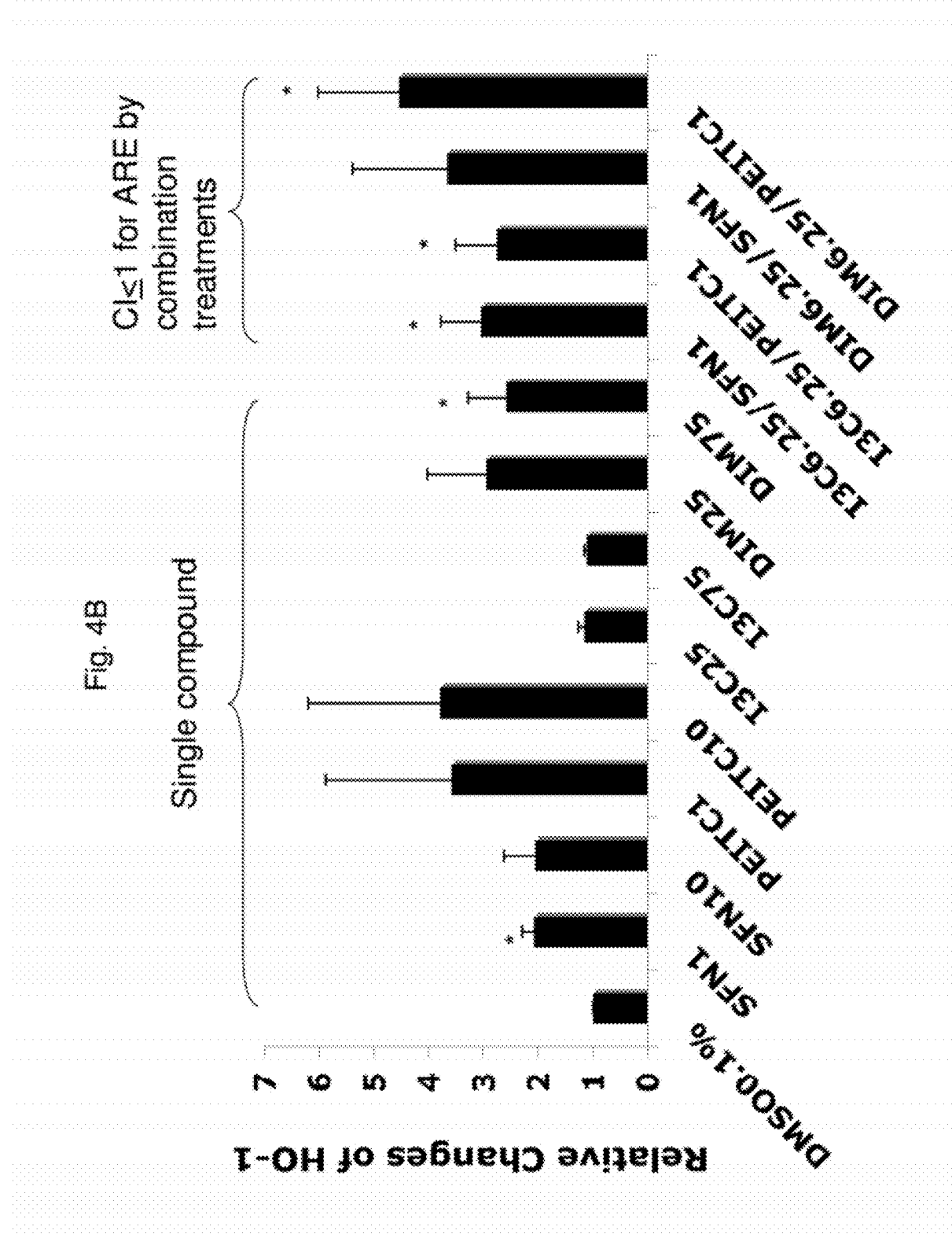
Figure 4C:
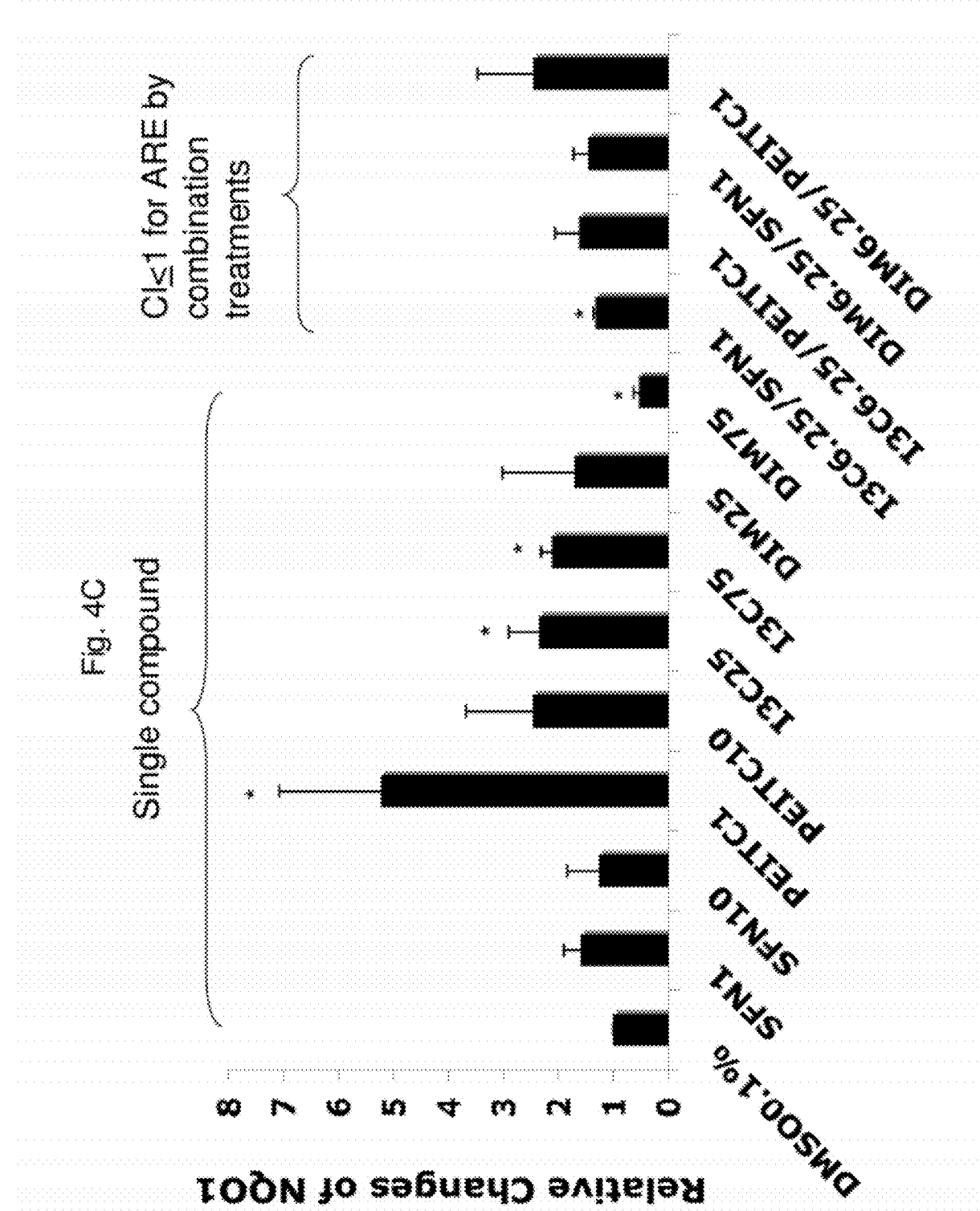
Figure 4D:
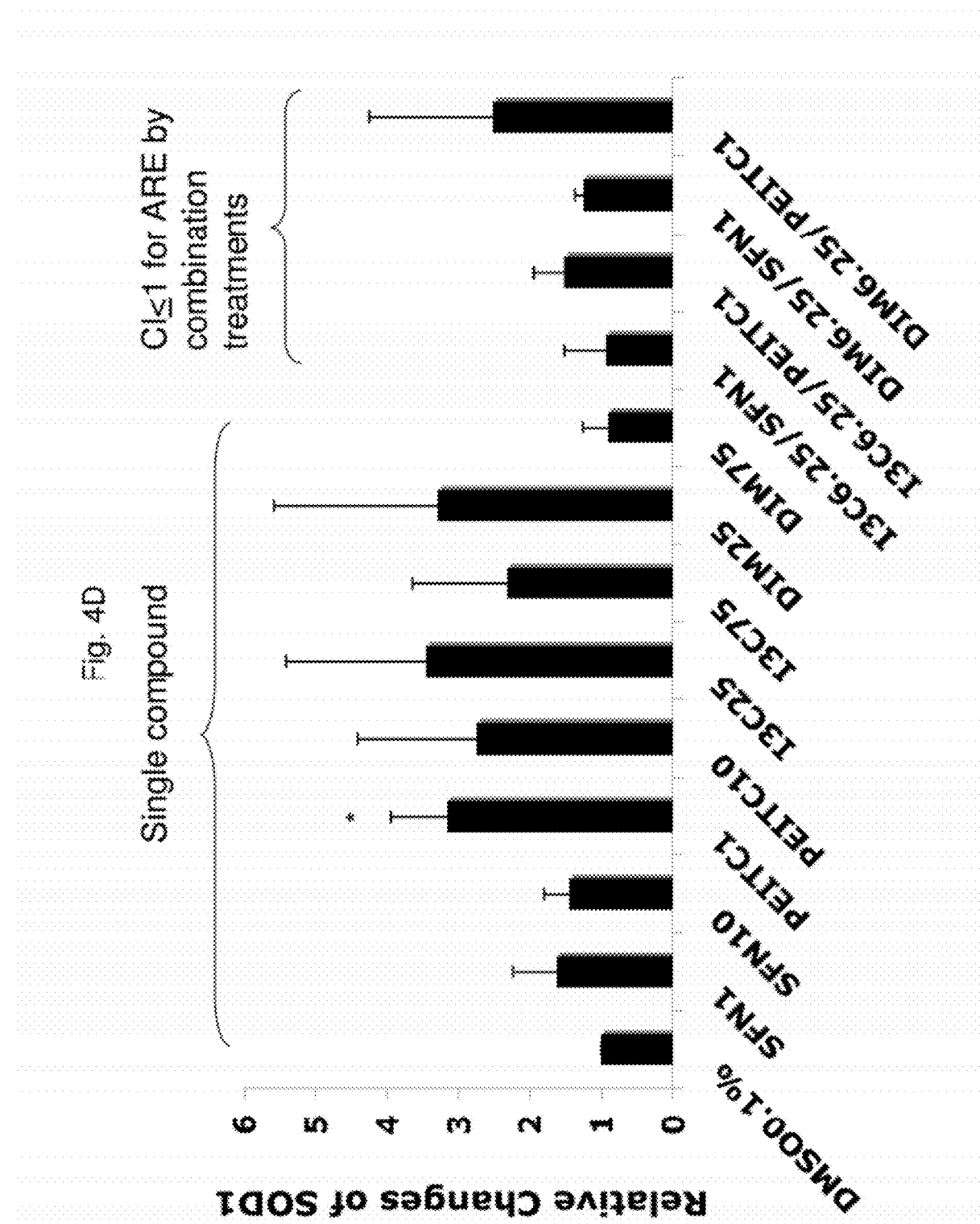

To confirm that the cells treated with the agents induced endogenous phase II DME and antioxidant genes, qPCR was conducted to quantify the mRNA expression. Values higher than 1 were considered positive in comparison with cells treated with control 0.1% DMSO. The results for the induction of Nrf2, phase DME and antioxidant genes are shown in FIG. 4. I3C alone at 25 µM did not show significant induction of Nrf2 and HO-1 mRNA (FIGS. 4A and 4B). On the other hand, 25 µM DIM showed about a 3 fold-induction for both of these genes. The higher dose, 75 µM DIM, induced only Nrf2 and HO-1 gene expression (FIGS. 4A and 4B), which was somehow not correlated to the dose-dependency activation of the ARE-luciferase above (FIG. 3), NQO1 gene expression was not significantly induced by SFN at any concentration, but it was greatly induced, by PEITC C even at a very low concentration of 1 µM (FIG. 4C). Similar to 10 µM PEITC, increasing the concentrations of I3C and DIM from 25 µM to 75 µM, did not enhance NQO1 gene expression any further (FIG. 4C). The time course study using SFN and PEITC at 6 h treatment indicated that the lower concentration of PEITC was a faster ARE inducer compared with SFN at 6 h. In addition, 1 µM PEITC induced higher ARE activity than 10 µM PEITC (data not shown). At 12 h, both SFN and PEITC at 10 µM had higher ARE induction than at the lower 1 µM concentration (data not shown). These observations are due to additional different mechanisms by which SFN and PEITC regulate gene expression, in addition to the common Nrf2-ARE mediated signaling pathway.

Among the combination treatments, 6.25 µM DIM with 1 µM PEITC had the greatest induction of SOD1 (FIG. 4D) and UGT1A1 (FIG. 4E), whereas 6.25 µM DIM with 1 µM SFN induced GSTm2 the most (FIG. 4F). These results confirmed the synergistic and additive effects of the combinations generated from the ARE-luciferase studies, respectively. In comparison with the other genes, with the same combinations, synergism was observed for HO-1, which was induced the most (FIG. 4B).

Example 5

Western Blot

FIG. 5 shows the selected protein biomarkers of Nrf2 and one of the Nrf2 downstream targets, SOD1, was examined using western blotting. It was hypothesized that the combination of low doses of indoles and ITCs could enhance Nrf2/ARE-mediated Nrf2 and Nrf2-target antioxidant enzymes such as SOD1. I3C and DIM alone at various concentrations was able to induce the protein levels of Nrf2 and SOD1 in a dosedependent manner (FIG. 5). The combinations of low doses of indoles and ITCs were also able to induce higher protein expression of SOD1 compared with the individual agent at higher concentrations and higher induction of Nrf2 and SOD1 proteins was also observed (FIG. 5, representative of three separate experiments with similar results), which corroborated the synergistic effects (CI<1) for the combination treatments identified in the ARE-luciferase assay (FIG. 3). In contrast, Nrf2 protein expression for DIM6.25/SFN1 treatment which was shown as additive using the CI calculation (FIG. 3), showed slightly less than 1 but yet the SOD1 expression was almost 2 fold compared with the 0.1% DMSO control. These results suggest that differential signaling pathways were activated by the indoles and the ITC at different concentrations with different combinations and that sometimes, endogenous gene expression would vary from the simple single promoter transcriptional reporter gene assay, so that the latter would provide a quick screen for potential vivo activities.

Example 6

Physicochemical Properties and Minimized Structures

The physicochemical properties of these compounds including polar surface area (PSA) and hydrophobicity expressed as ALogP (stands far atomic-based octanol/water partition coefficient) were tabulated in Table 1 above. SFN has a much lower ALogP, as compared to the other three compounds. This low ALogP 0.1647 correlates well with the highest PSA of 80.73 Å$^2$, while the other 3 compounds appear to be very hydrophobic.

When minimized structure of I3C was compared with DIM, there was a very good over-lay in their 31) conformation (FIGS. 6A-B). Similar observation was found in the minimized structures of SFN and PEITC when the N=C=S group was chosen for comparison (FIGS. 6C-D). In both of these indoles and ITCs cases, they are functionally different in terms of chemical properties. However, because they have common biological properties in activating. Nrf2-ARE pathway, such observations prompted us to further analyze the potential common pharmacophore present in the indoles and the ITCs. Indeed, a pharmacophoric triangle of similar bond length and the bond angle of 25° are present in all of these compounds (Table 2, and FIGS. 6A-D), suggesting potentially similar chemical property in activating Nrf2-ARE pathway and/or other pathways.

Example 7

Materials and Methods

This example describes general methods and materials used in Examples 8-15.

A. Reagents and Cell Culture

The DIM used in the study contains approximately 98% of DIM purchased from Sigma-Aldrich t St. Louis, Mo., USA), TRAMP C1 cells (provided by Dr. Barbara Foster, Department of Pharmacology and Therapeutics, Roswell Park Cancer institute, Buffalo. NY), originally derived from TRAMP prostate tumor, were cultured in Dulbecco's Modified Eagle's Medium (Invitrogen Corp., Carlsbad, Calif. U.S.A.) supplemented with 10% (V/V) fetal bovine serum (FBS) (Invitrogen Corp., Grand Island, N.Y., U.S.A.), penicillin 100 U/ml, and streptomycin 100 µg/ml (Invitrogen Corp., Grand Island, N.Y., U.S.A.), Cells were maintained in a humidified incubator with 5% CO2 at 37° C. Cells were seeded in 10 cm plates for 24 h and then treated with 0.1% DMSO (control) or different concentrations of DIM in 1% FBS containing medium for 5 days. The medium was changed every 2 days (20), B. Quantitative Real-Time PCR Assays (qPCR)

Total RNA were extracted from DIM treated TRAMP C1 cells and were reversed transcribed. The primers, DNMT1, DNMT3a, DNMT3b, NQO1, HO-1, GSTm1, UGT1a1 and control β-actin of qPCR are listed in Table 5 (Integrated DNA. Technologies, Coralville, Iowa, U.S.A.),

TABLE 5

Murine Primers for Quantitative Real-Time PCR

| Gene | Forward | Reverse |
| --- | --- | --- |
| β-actin | 5'-CGT TCA ATA CCC CAG CCA TG-3' (SEQ ID NO: 15) | 5'-GAC CCC GTC ACC AGA GTC C-3' (SEQ ID NO: 16) |
| DNMT1 | 5'-CCA AGC TCC GGA CCC TGG ATG TGT-3' (SEQ ID NO: 17) | 5'-CGA GGC CGG TAG TAG TCA CAG TAG-3' (SEQ ID NO: 18) |
| DNMT3a | 5'-GCA CCT ATG GGC TGC TGC GAA GAC G-3' (SEQ ID NO: 19) | 5'-CTG CCT CCA ATC ACC AGG TCG AAT G-3' (SEQ ID NO: 20) |
| DNMT3b | 5'-GTC TGC ACA CCA GAG ACC AGA G-3' (SEQ ID NO: 21) | 5'-TCA GAG CCA TTC CCA TCA TCT AC-3' (SEQ ID NO: 22) |

TABLE 5 -continued

Murine Primers for Quantitative Real-Time PCR

| Gene | Forward | Reverse |
|---|---|---|
| Nrf2 | 5'-AGC AGG ACA TGG AGC AAG TT-3' (SEQ ID NO: 23) | 5'-TTC TTT TTC CAG CGA GGA GA-3' (SEQ ID NO: 24) |
| NQO1 | 5'-AGC CCA GAT ATT GTG GCC G-3' (SEQ ID NO: 25) | 5'-CCT TTC AGA ATG GCT GGC AC-3' (SEQ ID NO: 26) |
| HO-1 | 5'-CCC ACC AAG TTC AAA CAG CTC-3' (SEQ ID NO: 27) | 5'-AGG AAG GGG GTC TTA GCC TC-3' (SEQ ID NO: 28) |
| GSTm1 | 5'-TTG TTC TGC CCA CGT TTC TCT AGT-3' (SEQ ID NO: 29) | 5'-TCT CAA ACT GGA TTC AGC AGG ACT-3' (SEQ ID NO: 30) |
| UGT1a1 | 5'-GAA ATT GCT GAG GCT TTG GGC AGA-3' (SEQ ID NO: 31) | 5'-ATG GGA GCC AGA GTG TGT GAT GAA-3' (SEQ ID NO: 32) |

The qPCR reactions were carried out with 1 µl cDNA product, 50 nM of each primer, and Power SYBR Green master mix (Applied Biosystems, Foster City, Calif., U.S.A.) in 10 µl reactions. The reactions were performed using an ABI Prism 7900HT sequence detection system; specificity of amplification was verified by first-derivative inciting curve analysis using the ABI software (SDS 2.3, Applied Biosystems, Foster City, Calif., U.S.A.). Relative quantification of gene expression profile was calculated using a ΔΔCt method. (RQ manager, Applied Biosystems, Foster City, C. CA, U.S.A.) as we have performed previously (Barve et al., *J Pharm Sci.*, 2008; 94: 4528-45). Three independent experiments were carried out showing similar results. The results are presented as mean±SD.

C. Animals

Female hemizygous C57BL/TGN TRAMP mice, line PB Tag 8247NG, and male C57BL/6 mice were purchased from The Jackson Laboratory (Bar Harbor, Me., U.S.A.). The animals were bred on the same genetic background C57BL/6 and maintained in the Laboratory Animal Service facility at Rutgers University. Housing and care of the animals was performed in accordance with the guidelines established by the University's Animal Research Committee consistent with the NIH Guidelines for the Care and Use of Laboratory Animals, Transgenic males for the studies were obtained as [TRAMP×C57BL/6] F1 or [TRAMP×C57BL/6] F2 offspring, Identity of transgenic mice was established by PCR-based DNA genotyping using the primers suggested by The Jackson Laboratory, as shown in Table 6 below. Throughout the experiment the animals were housed in a temperature-control led room (68-72° F.) with a 12 h light dark cycle, at a relative humidity of 45% to 55%.

D. Diet and Animal Study Design

DIM was obtained from Sigma-Aldrich (St. Louis, Mo., U.S.A.). MN-76A diets containing 1% DIM were prepared by Research Diets Inc. (New Brunswick, N.J., U.S.A.) and stored at −20° C. The dose was chosen based in part on studies reported previously Anderton et al., *Drug Metab Dispos.* 2004; 32: 632-8; and Xue et al., *J Nutr Biochem.* 2008; 19: 336-44). In our present study, 1% DIM was well-tolerated with these TRAMP mice. The control TRAMP males (n=19) received A1N-76A diets throughout the experiment while the treated TRAMP males received 1% DIM diet starting from eight weeks of age (n=9) as Group 1 (D-G1) and Group 2 (D-G2) starting from twelve weeks of age (n=8) (FIG. 12A). Fresh diets were added to the cages twice weekly.

TRAMP males were weighed weekly and the overall health of the animals was monitored on a regular basis. All mice were sacrificed at the age of 24 weeks by carbon dioxide euthanasia and the genitourinary apparatus (GU) consisting of the seminal vesicles, prostate, and bladder were isolated for further analyses (FIG. 12B).

E. Histopathology

The dorso-lateral prostate (n=5) was excised and fixed in 10% formalin for 24 b and then transferred to 70% ethanol for 24 h. After dehydration processing, and embedding with paraffin, tissue sections (4 µM) were cut from paraffin embedded prostate tissue and mounted on slides. The sections were stained with Hematoxylin and Eosin (H&E) to examine any neoplastic changes. Sections were evaluated by a histopathologist in a blinded fashion to classify prostatic intraepithelial neoplasia (PIN) lesion, as we have reported previously (8, 12, 13, 30), Lesions were classified as PIN I, PIN II, PIN III, and PIN IV (Park et al., *Am J Pathol.* 2002; 161: 727-35). For ease of classification, PIN I and PIN II were combined as low grade PIN (LG-PIN) while PIN III and PIN

TABLE 6

Confirmation of genotype of the TRAMP mice

| Gene | Primers |
|---|---|
| Tcrd Forward | 5'-CAA ATG TTG CTT GTC TGG TG-3' (SEQ ID NO: 33) |
| Tcrd Reverse | 5'-GTC AGT CGA GTG CAC AGT TT-3' (SEQ ID NO: 34) |
| SV1 | 5'-GGA CAA ACC ACA ACT ATG CAG TG-3' (SEQ ID NO: 35) |
| SV5 | 5'-CAG AGC AGA ATT GTG GAG TGG-3' (SEQ ID NO: 36) |

IV were combined as high grade PIN (HG-PIN) as we have performed previously (8, 12, 30, 31).

F. Immunohistochemistry (IHC) Staining Assay

Sections (4 μm) were cut from the paraffin embedded prostate tissue and mounted on glass slides. The slides Were deparafinized in xylene and antigen unmasking was performed by applying proteinase K digestion directly on the slides for 15 min. Endogenous peroxidase was blocked by incubating in 3% 14202 for 5 min, and ApopTag Plus Peroxidase In Situ Apoptosis Detection Kit (Millipore, Temecula, Calif., U.S.A.) was used to detect apoptotic cells. For detection of proliferative cells, monoclonal mouse anti-proliferating cell nuclear antigen (PCNA) antibody (Clone PC10, 1:50, Dako North America, Carpinteria, Calif., U.S.A.) was used (12). The staining was performed following as the manufacturer's protocols. Anti-5-methylcytosine (5-MC) mouse monoclone antibody (Clone 162 33 D3, 1:50, EMD Chemicals, Philadelphia, Pa., U.S.A.) was used to detect genome-wide methylated DNA. Vectastain ABC kit (Vector Laboratories, Inc., Burlingame, Calif., U.S.A.) was used to detect apoptotic cells by applying enzyme conjugated avidin, peroxidase substrate, and 3,3'-diaminobenzidine (DAB) to develop color for visualization.

G. Assessment of IHC Staining

Quantitation of IHC staining was done using the Aperio ScanScope® GL system according to the manufactures protocol (Aperio Technologies Inc., Vista, Calif., U.S.A.). This is a single-slide scanning system for digital pathological analysis of IHC of tumor samples to analyze the IHC-stained slides for the various cell cycle and apoptotic markers. The Aperio ImageScopoe software (v 10.1.3.2028) allowed the unbiased quantification and quantitative analysis of the IHC staining of biomarkers of prostate tumor samples obtained from untreated control versus the treated TRAMP mice.

H. Western Blot

The TRAMP C1 cells or dorso-lateral prostate tissues collected from treated and control groups were pooled and homogenized with RIPA buffer (Cell Signaling Technology, Danvers, Mass., U.S.A.) and 10 μg/ml protease inhibitor cocktail (EMD Chemicals, Philadelphia, Pa., U.S.A.). Protein (20 μg) was loaded onto 4-15% SDS-PAGE (Bio-Rad Laboratories, Hercules, Calif., U.S.A.). After separation by SDS-PAGE, the protein was transferred onto nitrocellulose membrane (Millipore Corp., Billerica, Mass., U.S.A.), and then was blocked in 5% bovine serum albumin (BSA) (Fisher Scientific, Fair Law, J. U.S.A.) in tris buffer saline tween-20 (TBST) solution for 1 h. Membranes were probed using the different mono- or polyclonal-antibodies (1:1000) overnight at 4"C. Blots were washed with TBST solution for 15 min 4 times and incubated with the respective secondary antibodies for 1 hr. After washing min 4 times with TBST solution, the immunoreactive bands were determined by adding SuperSignal West Femto mix (1:1 mix of stable peroxide buffer and luminol/enhancer solution (Thermo Scientific, Rockford, Ill., U.S.A.) to detect immunoreactive bands. The bands were visualized and quantified by BioRad ChemiDoc XRS system (Hercules, Calif., U.S.A.). The primary antibodies used were β-actin, Nrf2, NQO1 (Santa Cruz Biotechnology, Santa Cruz, Calif., U.S.A.), HDAC1, HDAC2, HDAC3, HDAC4 (Cell Signaling Technology Inc., Danvers Mass., U.S.A.), HDAC8 (Proteintech Group Inc., Chicago, Ill., U.S.A.) and DNMT1, DNMT3a, DNMT3b (Imgenex, San Diego, Calif., U.S.A.). The secondary antibodies used were goat polyclonal IgG for β-actin and NQO1, rabbit polyclonal IgG for Nrf2, HDAC1, HDAC2, HDAC3, HDAC4 and HDAC8, and mouse polyclonal IgG for DNMT1, DNMT3a, DNMT3b (Santa Cruz Biotechnology, Santa Cruz, Calif., U.S.A.), I. DNA Extraction and Bisulfite Genomic Sequencing Genomic DNA was isolated from the control or DIM treated TRAMP C1 cells and TRAMP dorso-lateral prostate tissues collected from control and DIM treated groups pooled and homogenized using the DNeasy tissue kit (Qiagen, Valencia, Calif., U.S.A.). The genomic DNAs were extracted and subjected to bisulfite conversion carried out using 750 ng of genomic DNA and applying to EZ DNA Methylation Gold Kits (Zymo Research Corp., Orange, Calif., U.S.A.) following the manufacturer's instructions. The converted DNA was amplified by PCR utilizing Platinum PCR SuperMix (Invitrogen, Grand Island, N.Y., U.S.A.) with a set of specific primers, forward: 5'-AGT TAT GAA GTA GTA GTA AAA A-3' (SEQ ID NO: 37) and reverse: 5'-AAT ATA ATC TCA TAA AAC CCC AC-3' (SEQ ID NO: 38), amplifying the first five CpGs located between −1266 and −1086 of the promoter region of Nrf2 with the translation initiation site defined as +1 (14, 20). Gel extraction using Qiaquick™ gel extraction kit (Qiagen, Valencia, Calif., U.S.A.) were used to purify the PCR products, then cloned into pCR4 TOPO vector using a TOPO™ TA Cloning kit (Invitrogen, Grand Island, N.Y., U.S.A.), Plasmids DNA from at least twenty colonies per for treatment were prepared using QIAprep Spin Miniprep Kit (Qiagen, Valencia Calif., U.S.A.) and sequenced (Genwiz, Piscataway, N.J., U.S.A.).

J. Methylation DNA Immunoprecipitation (MeDIP) Analysis

Genomic DNA (8 μg each) extracted from control and DIM treated TRAMP C1 cells were used for the MeDIP analysis, analogous to other chromatin immuno-precipitation (ChIP) analysis. The DNAs were adjusted to 150 μl using TE buffer in DNA. LoBind tubes. DNAs were fragmented by sonication on ice-water using a Bioruptor sonicator (Diagnode Inc., Sparta, N.J., U.S.A.) and the size of sheared DNA fragment (around 300 to 500 bp) was checked by gel electrophoresis. Inputs from each sample contained around one-tenth of the amount of fragmented DNAs; the remaining DNA were applied for denaturing for 10 min, and immunoprecipitation (IP) in 1×IP buffer (10 mM sodium phosphate pH 7.0, 140 mM NaCl, 0.25% Triton X-100) using anti-methylcytosine antibody (anti-mecyt, purchased from Anaspec, Fremont, Calif., U.S.A.), and anti-cMyc as a negative control antibody (Santa Cruz. Santa Cruz, Calif.) for 2 his at 4"C, respectively. After the incubation, 30 μl magnetic beads (Cell signaling, Boston. MA) were added, and rotated at 4'C for another 2 hr. The pulled-down DNA-beads complex were washed four times using ice cold IP buffer and then digested with proteinase K at 50"C overnight. Precipitated DNA was purified using miniprep kit from Qiagen Valencia Calif., U.S.A.). The inputs and precipitated DNA were used as templates for PCR amplification of Nrf2 promoter region position from −1092 to −1190 covering the first 5 CpGs as described previously (14, 20). A forward primer 5'-GAG GTC ACC ACA ACA CGA AC-3' (SEQ ID NO: 39) and a reverse primer 5'-ATC TCA TAA GGC CCC ACC TC-3' (SEQ ID NO: 40) were used to amplify the Nrf2 fragment. PCR was performed using Platinum PCR superMix (Invitrogen, Grand Island, N.Y., U.S.A.). The PCR products were separated by agarose gel electrophoresis and visualized by ethidium bromide (EB) staining using a Gel Documentation 2000 system (Bio Rad Laboratories. Hercules, Calif., U.S.A.), K. Statistical Analysis Results were presented as means±standard deviation (SD). Data was analyzed using SPSS software (version 17, IL., U.S.A.), and nonparametric statistical test Mann-Whitney U (35) was performed for in vivo animal study. Box-plots presentation were used: the upper boundary of the box represents the 75th percentile while the lower boundary of the box represents 25th percentile of the data distribution, the horizontal line within each box represents the median value and the error bars represent the 95% confidence intervals. The student's Nest was used to determine the statistical differences for the in vitro study.

Example 8

Effects of DIM-Supplemented Diet and Overall Health of TRAMP Mice

The overall health of all the mice was monitored during the study period and found to be in good health. All mice were weighed and checked weekly during the course of this study. No significant change in the body weights of all the mice was found throughout the study period. In addition, the liver, kidney, and spleen of the DIM treatment and control groups were collected and weighed after the animals were sacrificed and there was no significant change on the weights of these organs. There was no specific observable sign of toxicity.

Example 9

DIM-Supplemented Diet Inhibited TRAMP Prostate Tumorigenesis

DIM treated groups (D-G1 and D-G2, $p<0.05$) showed statistically significant decrease in the wet GUT weight as compared to the non-treated control group, as shown in FIG. 12B. Seven control untreated mice were found to have hyperplasia and lesions of the prostate tissues and or the seminal vesicles and six mice were found to have primary palpable prostate tumors, as shown in Table 3 above. DIM decreased the incidence of palpable tumor and metastasis. Six untreated control mice had primary palpable tumors and five were associated with distinct lymph nodes metastases with no lung or liver metastasis. The remaining mice in the control group were found to have either HG-PIN or carcinoma by histological analysis, as shown in FIG. 12C. DIM significantly reduced the incidence of palpable tumor in D-G2 ($p<0.05$) and lymph nodes metastasis in both D-G1 and D-G2 ($p<0.05$), as shown in Table 3 above. In D-G1, although one mouse had a palpable tumor that was confirmed histologically as carcinoma, overall the mice treated with DIM starting from 8-week of age (D-G1) showed 60% incidence, of LG-PIN and 20% of HG-PIN, as shown in FIG. 12C. In contrast, mice treated with DIM starting from 12-week of age (D-G2) had 80% HG-PIN and 20% LG-PIN and no carcinoma, as shown in FIG. 12C. Compared to the control group, DIM treated mice had an overall lower tumor incidence and PIN lesions (FIG. 12C), indicating that DIM suppresses PCa tumor formation and progression. DIM had no suppression effect of SV-40 transgene expression (data not shown).

Example 10

DIM Inhibited Cell Proliferation and Enhanced Apoptosis in TRAMP Prostate Tissues PCNA is an auxiliary protein for DNA polymerase known to be cell cycle regulated. TRAMP males treated with DIM for 16 (D-G1) or 12 (D-G2) weeks resulted in significantly lower levels of PCNA staining 0.042, 0.030, respectively) measured by IHC analysis, as shown in FIG. 13A. The percent of apoptotic cells in the dorso-lateral prostates of the TRAMP males fed with DIM-supplemented diet in D-G1 and D-G2 was significantly higher than the control group ($p<0.001$), as shown in FIG. 13B. Moreover, the percent of apoptotic cells in D-G1 was significantly higher than in D-G2 ($p=0.029$) as shown in FIG. 13B. These results indicate that the tumor inhibitory effect of DIM is correlated in part with increased apoptosis and suppressed proliferation of prostatic epithelial tumor cells. DIM induced protein expression of anti-oxidative stress genes Nrf2 and Nrf2-target gene NQO1 in TRAMP prostate tissues FIG. 7 shows that DIM induced Nrf2 proteins expression in both O-G1 and D-G2 in the dorso-lateral prostate tissues of the TRAMP mice. Moreover. NQO1, an Nrf2-targeted downstream antioxidant enzyme, was also induced by DIM in both D-G1 and D-G2 (FIG. 7). Nrf2 and NQO1 protein expression in the prostate tumor samples from the control untreated TRAMP mice was undetectable (FIG. 7), consistent with our previous reported findings.

Example 11

DIM Suppressed Global CpG Methylation Staining by 5-MC in TRAMP Prostate Tissues Aberrant CpG DNA methylation is acquired during carcinogenesis. 5-methylcytosine (5-MC) is generated when DNA methyltransferases (DNMT) add a methyl group to the 5-carbon atom of the DNA base cytosine (C). In mammalian cells, 5-MC is found predominantly within CpG dinucleotides. Aberrant hypermethylation of CpG islands of many tumor suppressor genes has been linked to the development of cancer. Furthermore, 5-MC has been proposed to be a critical clinical biomarker for the diagnosis of cancer and tumors formation. FIG. 8A shows that DIM significantly decreased 5-MC IHC staining of the prostate tissue in both group D-G1 and D-G2 ($p<0.001$, respectively). In addition, the percentage of 5-MC in D-G1 was significantly lower than in D-G2 ($p<0.05$).

Example 12

DIM Demethylated the First Five CpGs of the Nrf2 Gene Promoter of TRAMP Prostate Tissues The first five CpGs on the Nrf2 gene promoter region are hypermethylated in TRAMP prostate rumors and in TRAMP C1, but not M normal prostate tissues. In the present study, BGS analysis showed that, in TRAMP prostate tissues or tumors, the first five CpGs were hypermethylated in the control group (FIG. 8B. Control, 98% methylation). In contrast to the control group, DIM treatment groups of D-G1/D-G2 had significantly lower methylation of the first five CpGs of Nrf2 (FIG. 4B, 37.6% 54.4%, respectively, $p<0.001$), indicating that DIM inhibits the CpG methylation of the first 5 CpGs of Nrf2 promoter, which enhances the transcription of Nrf2 in the TRAMP prostate tissues. Furthermore, comparing the two DIM treated groups, D-G1 showed a significantly lower methylation level of the first 5 CpGs of Nrf2 than D-G2 ($p<0.05$).

Example 13

DIM Decreased the Hypermethylation of First 5 CpGs in the Promoter Region of Nrf2 Gene and Enhanced Expression of Nrf2 and Nrf2-Target Genes in TRAMP C1-Cells To further confirm the in vivo results in TRAMP mice above, BGS was performed to test if DIM could reverse the methylation status of the first 5 CpGs in the promoter region of Nrf2 genes as observed in the TRAMP mice above. In agreement with the in vivo results, the first 5 CpGs were hypermethylated in TRAMP C1 cells (FIG. 9A, 96.8% methylated). Treatment of cells with 2.5 μM or 5 μM of DIM for 5 days, significantly decreased the methylation status of these 5 CpGs on the Nrf2 promoter region in a dose-dependent manner (FIG. 5A, 73.7% and 55.8% methylation, respectively. Fisher's exact test, $p<0.001$).

MeDIP/ChIP analysis has been commonly used to enrich the methylated CpG DNA in an unbiased manner. Anti-mecyt antibody which binds specifically to the methylated cytosine (MC) was used to immunoprecipitate (IP) the genomic. DNA harvested from control and DIM-treated TRAMP C1 cells. The IP DNA was purified and used for PCR to amplify the Nrf2 promoter region containing the first 5 CpGs. MeDIP results showed that DIM reduced the methylated. DNA bound by anti-mecyt antibody to the first 5 CpGs of Nrf2 gene promoter, as shown in FIGS. 9B and 9C.

Example 14

DIM Induced Anti-Oxidative Stress Genes Nrf2 and Nrf2-Target Genes and Protein Expression in TRAMP C1 Cells DIM enhanced the mRNA expression of Nrf2 and Nrf2-target genes NQO1 and GSTm1 in TRAMP C1 cells (FIG. 10A), which was originally derived from TRAMP prostate tumor. In agreement with the results of mRNA expressions. Nrf2 and Nrf2-target gene, NQO1, protein levels were significantly induced in TRAMP C1 cells treated with DIM, as shown in FIG. 10R These results suggest that DIM is able to modify the epigenetic status of CpG methylation of Nrf2 (from above), and restores Nrf2 and Nrf2-target genes mRNA and protein expressions in TRAMP C1 cells in vitro, which substantiate the in vivo results in TRAMP prostate tissues shown above.

Example 15

DIM Suppressed DNA Methyltransferases (DNMTs) Expression in TRAMP C1 Cells

The in vivo results from the TRAMP mice and in vitro results from TRAMPC1 cells above clearly show that DIM supplementation in the diet and DIM treatment of TRAMP C1 cells reduced the CpG methylation status of the Nrf2 gene promoter region and decreased global CpG methylation. To elucidate the potential molecular epigenetic mechanism by which DIM exerts its DNA hypomethylation effect, the effect of DIM on DNMTs and HDACs mRNA and protein expression was examined. FIG. 14A shows the effect of DIM on the mRNA expression of DNMT1, DNMT3a, and DNMT3b quantitated by qPCR in TRAMP C1 cells. DIM significantly suppressed the mRNA expression of DNMT1 at both 5 μM and 10 μM concentrations ($p<0.05$) whereas DNMT3a was suppressed by DIM at 5 μM concentration more significantly ($p<0.05$). To corroborate the mRNA expression of DNMT1, 3a and 3b (FIG. 14A), western blotting show DIM suppressed the protein levels of DNMT1, and DNMT3b in TRAMP C1 cells, as shown in FIG. 14B). Furthermore, western blotting also shows that DIM could suppress the protein expression of HDAC2 and HDAC3 in TRAMP C1 cells, as shown in FIG. 14B.

What is claimed is:

1. A method for inducing expression of anti-oxidative stress enzymes in a subject in need thereof, comprising administering to the subject a therapeutically effective amount of a demethylating agent comprising a phytochemical that induces the expression of Nrf2 and Nrf2-mediated genes expressing anti-oxidative stress enzymes, wherein said phytochemical is selected from the group consisting of indoles, isothiocyanates, and combinations of these.

2. The method of claim 1, wherein the subject has a disease or disorder characterized by decreased expression of anti-oxidative stress enzymes, wherein said disease or disorder is selected from inflammation, diabetes, multiple sclerosis, amyotrophic lateral sclerosis, Parkinson's disease, Alzheimer's disease, atherosclerosis, heart failure, myocardial infarction, Schizophrenia, Bipolar disorder, fragile X syndrome, Sickle Cell Disease, and chronic fatigue syndrome.

3. The method of claim 1, wherein the anti-oxidative stress enzymes are selected from the group consisting of GST, NQO1, SOD1, and HO-1.

4. The method of claim 1, wherein the isothiocyanates are selected from the group consisting of phenethyl isothiocyanate and sulforaphane.

5. The method of claim 1, wherein the phytochemical comprises one or more indoles.

6. The method of claim 1, wherein the phytochemical comprises a compound selected from the group consisting of 3,3'-diindolylmethane, indole-3-carbinol, and combinations of these.

7. The method of claim 1, wherein the phytochemical comprises 3,3'-diindolylmethane.

8. The method of claim 5, wherein the therapeutically effective amount of 3,3'-diindolylmethane is in the range of from about 1.62 mg/kg to about 3.24 mg/kg per day.

* * * * *